US012023379B2

(12) United States Patent
Selvaraj

(10) Patent No.: US 12,023,379 B2
(45) **Date of Patent: *Jul. 2, 2024**

(54) IMMUNOSTIMULATORY COMPOSITIONS, PARTICLES, AND USES RELATED THERETO

(71) Applicant: Emory University, Atlanta, GA (US)

(72) Inventor: Periasamy Selvaraj, Lilburn, GA (US)

(73) Assignee: Emory University, Atlanta, GA (US)

( * ) Notice: Subject to any disclaimer, the term of this patent is extended or adjusted under 35 U.S.C. 154(b) by 560 days.

This patent is subject to a terminal disclaimer.

(21) Appl. No.: 17/132,320

(22) Filed: Dec. 23, 2020

(65) Prior Publication Data

US 2021/0154291 A1 May 27, 2021

Related U.S. Application Data

(63) Continuation of application No. 15/833,769, filed on Dec. 6, 2017, now Pat. No. 10,987,419, which is a continuation of application No. 14/374,729, filed as application No. PCT/US2013/024355 on Feb. 1, 2013, now abandoned.

(60) Provisional application No. 61/594,754, filed on Feb. 3, 2012.

(51) Int. Cl.

| | |
|---|---|
| ***C07K 16/28*** | (2006.01) |
| ***A61K 39/00*** | (2006.01) |
| ***A61K 39/385*** | (2006.01) |
| ***A61K 39/39*** | (2006.01) |
| ***A61K 39/395*** | (2006.01) |
| ***A61P 35/00*** | (2006.01) |

(52) U.S. Cl.

CPC ........ *A61K 39/385* (2013.01); *A61K 39/0011* (2013.01); *A61K 39/001102* (2018.08); *A61K 39/001106* (2018.08); *A61K 39/001124* (2018.08); *A61K 39/001129* (2018.08); *A61K 39/00117* (2018.08); *A61K 39/001172* (2018.08); *A61K 39/001173* (2018.08); *A61K 39/001182* (2018.08); *A61K 39/00119* (2018.08); *A61K 39/001191* (2018.08); *A61K 39/001193* (2018.08); *A61K 39/001194* (2018.08); *A61K 39/001195* (2018.08); *A61K 39/39* (2013.01); *A61K 2039/515* (2013.01); *A61K 2039/5152* (2013.01); *A61K 2039/5258* (2013.01); *A61K 2039/55511* (2013.01); *A61K 2039/55516* (2013.01); *A61K 2039/55522* (2013.01); *A61K 2039/55533* (2013.01); *A61K 2039/55538* (2013.01); *A61K 2039/55561* (2013.01); *A61K 2039/55572* (2013.01); *A61K 2039/6018* (2013.01); *A61K 2039/62* (2013.01); *A61K 2039/627* (2013.01)

(58) Field of Classification Search

None

See application file for complete search history.

(56) References Cited

U.S. PATENT DOCUMENTS

| | | | | |
|---|---|---|---|---|
| 10,987,419 B2 * | 4/2021 | Selvaraj | A61K 39/0011 | |
| 2002/0009468 A1 * | 1/2002 | Selvaraj | A61K 39/0005 | 424/277.1 |
| 2002/0018767 A1 * | 2/2002 | Lee | A61K 39/0011 | 435/366 |
| 2002/0039573 A1 * | 4/2002 | Cheever | A61P 35/00 | 435/372 |
| 2002/0162123 A1 * | 10/2002 | Chang | A01K 67/0271 | 800/18 |
| 2003/0082143 A1 * | 5/2003 | Larocca | A61P 37/02 | 435/456 |
| 2003/0105054 A1 * | 6/2003 | Wagner | A61K 38/208 | 514/44 R |
| 2005/0272114 A1 * | 12/2005 | Darzins | C12Q 1/34 | 530/324 |
| 2007/0243159 A1 * | 10/2007 | Selvaraj | A61K 39/0011 | 424/277.1 |
| 2007/0269455 A1 * | 11/2007 | Segal | A61K 39/39 | 424/274.1 |
| 2009/0217401 A1 * | 8/2009 | Korman | C07K 16/28 | 536/23.53 |
| 2009/0285860 A1 * | 11/2009 | Martuza | A61K 39/0011 | 435/375 |
| 2010/0266617 A1 * | 10/2010 | Carven | A61P 37/04 | 435/69.6 |
| 2011/0183437 A1 * | 7/2011 | Yarden | C07K 16/32 | 436/501 |
| 2012/0064035 A1 * | 3/2012 | Hadden | A61P 17/00 | 424/85.2 |

(Continued)

OTHER PUBLICATIONS

Brunschwig et al. (1995) Glycosylphosphatidylinositol-modified murine B7-1 and B7-2 retain costimulator function. J Immunol 155: 5498-5505.*

De Giovanni et al. 2004 Immunoprevention of HER-2/neu Transgenic Mammary Carcinoma through an Interleukin 12-Engineered Allogeneic Cell Vaccine. Cancer Research 64: 4001-4009.*

Kubin et al. (1994) Interleukin 12 synergizes with B7/CD28 interaction in inducing efficient proliferation and cytokine production of human T cells. J. Exp. Med. 180: 211-222.*

Putzer et al. (1997) Interleukin 12 and B7-1 costimulatory molecule expressed by an adenovirus vector act synergistically to facilitate tumor regression. Proc Natl Acad Sci USA 94: 10889-10894.*

Chen et al. (1996) Tumor Cells Transfected with B7-1 and Interleukin-12 cDNA Induce Protective Immunity. Ann. NY Acad. Sci. 795: 325-327.*

(Continued)

*Primary Examiner* — Ilia I Ouspenski

(74) *Attorney, Agent, or Firm* — Meunier Carlin & Curfman LLC

(57) ABSTRACT

In some embodiments, described herein is a method of tumor treatment or tumor vaccination. The method generally comprises applying to a human being in need thereof a tumor therapeutic composition or tumor vaccine defined herein. The tumor therapeutic composition or tumor vaccine can be produced by protein transfer of glycosyl-phosphatidylinositol (GPI)-anchored immunostimulatory or costimulatory molecules.

6 Claims, 6 Drawing Sheets

Specification includes a Sequence Listing.

(56) References Cited

U.S. PATENT DOCUMENTS

2013/0295110 A1* 11/2013 Binder .................... A61P 35/00 424/277.1
2013/0323249 A1* 12/2013 Zhou ....................... A61P 35/00 530/387.3

OTHER PUBLICATIONS

Cimino et al. (2004) Cancer Vaccine Development: Protein Transfer of Membrane-Anchored Cytokines and Immunostimulatory Molecules. Immunologic Research 29: 231-240.*
Coughlin et al. (1995) B7-1 and interleukin 12 synergistically induce effective antitumor immunity. Cancer Res. 55: 4980-4987.*
Komata et al. (1997) B7-1 (CD80)-transfected human glioma cells and interleukin-12 directly stimulate allogeneic CD8+ T cells. J. Immunother. 20: 256-264 (Abstract only).*
Nagarajan et al. (2002) Glycolipid-anchored IL-12 Expressed on Tumor Cell Surface Induces Antitumor Immune Response. Cancer Research 62: 2869-2874.*
Pan et al. (Feb. 14, 2012) Cancer Immunotherapy Using a Membrane-bound Interleukin-12 with B7-1 Transmembrane and Cytoplasmic Domains. Molecular Therapy (2012) 20: 927-937.*
Masuda et al. (2003) Epigallocatechin-3-gallate Inhibits Activation of HER-2/neu and Downstream Signaling Pathways in Human Head and Neck and Breast Carcinoma Cells. Clinical Cancer Research 9: 3486-3491.*
Johnson et al. (2020) Head and neck squamous cell carcinoma. Nature Reviews—Disease Primers 6(1): 92 (22 pages).*
Wang et al. (2006) B7-1-HSA (CD80-CD24), a recombinant hybrid costimulatory molecule retains ligand binding and costimulatory functions. Immunology Letters 105: 185-192.*
Topalian et al. (2012) Safety, Activity, and Immune Correlates of Anti-PD-1 Antibody in Cancer. N Engl J Med 366: 2443-2454.*
Communication Pursuant to Article 94(3) EPC issued for Application No. 18196067.5, dated Nov. 14, 2022.

* cited by examiner

SEQUENCE LISTING

<160> NUMBER OF SEQ ID NOS: 8

<210> SEQ ID NO 1
<211> LENGTH: 288
<212> TYPE: PRT
<213> ORGANISM: Artificial
<220> FEATURE:
<223> OTHER INFORMATION: Synthetic

<400> SEQUENCE: 1

Met Gly His Thr Arg Arg Gln Gly Thr Ser Pro Ser Lys Cys Pro Tyr
1 5 10 15

Leu Asn Phe Phe Gln Leu Leu Val Leu Ala Gly Leu Ser His Phe Cys
20 25 30

Ser Gly Val Ile His Val Thr Lys Glu Val Lys Glu Val Ala Thr Leu
35 40 45

Ser Cys Gly His Asn Val Ser Val Glu Glu Leu Ala Gln Thr Arg Ile
50 55 60

Tyr Trp Gln Lys Glu Lys Lys Met Val Leu Thr Met Met Ser Gly Asp
65 70 75 80

Met Asn Ile Trp Pro Glu Tyr Lys Asn Arg Thr Ile Phe Asp Ile Thr
85 90 95

Asn Asn Leu Ser Ile Val Ile Leu Ala Leu Arg Pro Ser Asp Glu Gly

-continued

```
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285


<210> SEQ ID NO 2
<211> LENGTH: 208
<212> TYPE: PRT
<213> ORGANISM: Artificial
<220> FEATURE:
<223> OTHER INFORMATION: Synthetic

<400> SEQUENCE: 2

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
```

-continued

```
            180                 185                 190

Gln Thr Phe Asn Trp Asn Thr Thr Lys Gln Glu His Phe Pro Asp Asn
        195                 200                 205


<210> SEQ ID NO 3
<211> LENGTH: 126
<212> TYPE: PRT
<213> ORGANISM: Artificial
<220> FEATURE:
<223> OTHER INFORMATION: Synthetic

<400> SEQUENCE: 3

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Ala
            100                 105                 110

Gln Ile Tyr Val Ile Asp Pro Glu Pro Cys Pro Asp Ser Asp
        115                 120                 125


<210> SEQ ID NO 4
<211> LENGTH: 607
<212> TYPE: PRT
<213> ORGANISM: Artificial
<220> FEATURE:
<223> OTHER INFORMATION: Synthetic

<400> SEQUENCE: 4

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160
```

-continued

```
Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
```

-continued 580 585 590

Lys Phe Pro Asp Glu Glu Gly Ala Cys Gln Pro Cys Pro Ile Asn
595 600 605

<210> SEQ ID NO 5
<211> LENGTH: 214
<212> TYPE: PRT
<213> ORGANISM: Artificial
<220> FEATURE:
<223> OTHER INFORMATION: Synthetic

<400> SEQUENCE: 5

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 6
<211> LENGTH: 55
<212> TYPE: PRT
<213> ORGANISM: Artificial
<220> FEATURE:
<223> OTHER INFORMATION: Synthetic

<400> SEQUENCE: 6

Gly Thr Ser His Leu Val Lys Cys Ala Glu Lys Glu Lys Thr Phe Cys
1 5 10 15

Val Asn Gly Gly Glu Cys Phe Met Val Lys Asp Leu Ser Asn Pro Ser
20 25 30

Arg Tyr Leu Cys Lys Cys Pro Asn Glu Phe Thr Gly Asp Arg Cys Gln
35 40 45

Asn Tyr Val Met Ala Ser Phe
50 55

-continued

<210> SEQ ID NO 7
<211> LENGTH: 2254
<212> TYPE: DNA
<213> ORGANISM: Artificial
<220> FEATURE:
<223> OTHER INFORMATION: Synthetic

<400> SEQUENCE: 7

```
aaggggaggt aaccctggcc cctttggtcg gggccccggg cagccgcgcg ccccttccca      60
cggggccctt tactgcgccg cgcgcccggc ccccacccct cgcagcaccc cgcgccccgc     120
gccctcccag ccgggtccag ccggagccat ggggccggag gatatcccgc agtgagcacc     180
atggagctgg cggccttgtg ccgctggggg ctcctcctcg ccctcttgcc ccccggagcc     240
gcgagcaccc aagtgtgcac cggcacagac atgaagctgc ggctccctgc cagtcccgag     300
acccacctgg acatgctccg ccacctctac cagggctgcc aggtggtgca gggaaacctg     360
gaactcacct acctgcccac caatgccagc ctgtccttcc tgcaggatat ccaggaggtg     420
cagggctacg tgctcatcgc tcacaaccaa gtgaggcagg tcccactgca gaggctgcgg     480
attgtgcgag gcacccagct ctttgaggac aactatgccc tggccgtgct agacaatgga     540
gacccgctga acaataccac ccctgtcaca ggggcctccc caggaggcct gcgggagctg     600
cagcttcgaa gcctcacaga gatcttgaaa ggaggggtct tgatccagcg gaacccccag     660
ctctgctacc aggacacgat tttgtggaag gacatcttcc acaagaacaa ccagctggct     720
ctcacactga tagacaccaa ccgctctcgg gcctgccacc cctgttctcc gatgtgtaag     780
ggctcccgct gctggggaga gagttctgag gattgtcaga gcctgacgcg cactgtctgt     840
gccggtggct gtgcccgctg caaggggcca ctgcccactg actgctgcca tgagcagtgt     900
gctgccggct gcacgggccc caagcactct gactgcctgg cctgcctcca cttcaaccac     960
agtggcatct gtgagctgca ctgcccagcc ctggtcacct acaacacaga cacgtttgag    1020
tccatgccca atcccgaggg ccggtataca ttcggcgcca gctgtgtgac tgcctgtccc    1080
tacaactacc tttctacgga cgtgggatcc tgcaccctcg tctgccccct gcacaaccaa    1140
gaggtgacag cagaggatgg aacacagcgg tgtgagaagt gcagcaagcc ctgtgcccga    1200
gtgtgctatg gtctgggcat ggagcacttg cgagaggtga gggcagttac cagtgccaat    1260
atccaggagt ttgctggctg caagaagatc tttgggagcc tggcatttct gccggagagc    1320
tttgatgggg acccagcctc caacactgcc ccgctccagc cagagcagct ccaagtgttt    1380
gagactctgg aagagatcac aggttaccta tacatctcag catggccgga cagcctgcct    1440
gacctcagcg tcttccagaa cctgcaagta atccggggac gaattctgca caatggcgcc    1500
tactcgctga ccctgcaagg gctgggcatc agctggctgg ggctgcgctc actgagggaa    1560
ctgggcagtg gactggccct catccaccat aacacccacc tctgcttcgt gcacacggtg    1620
ccctgggacc agctctttcg gaacccgcac caagctctgc tccacactgc caaccggcca    1680
gaggacgagt gtgtgggcga gggcctggcc tgccaccagc tgtgcgcccg agggcactgc    1740
tggggtccag ggcccaccca gtgtgtcaac tgcagccagt tccttcgggg ccaggagtgc    1800
gtggaggaat gccgagtact gcaggggctc cccagggagt atgtgaatgc caggcactgt    1860
ttgccgtgcc accctgagtg tcagccccag aatggctcag tgacctgttt tggaccggag    1920
gctgaccagt gtgtggcctg tgcccactat aaggaccctc ccttctgcgt ggcccgctgc    1980
cccagcggtg tgaaacctga cctctcctac atgcccatct ggaagtttcc agatgaggag    2040
ggcgcatgcc agccttgccc catcaactgc acccactcct gtgtggacct ggatgacaag    2100
```

-continued

```
ggctgccccg ccgagcagag agccagccct ctgacggaat tccttgaaaa tggtgggaca   2160

tccttatcag agaaaacagt tcttctgctg gtgactccat ttctggcagc agcctggagc   2220

cttcatccct aacagaaggc caaggggccc tccg                               2254


<210> SEQ ID NO 8
<211> LENGTH: 22
<212> TYPE: DNA
<213> ORGANISM: Artificial
<220> FEATURE:
<223> OTHER INFORMATION: Synthetic

<400> SEQUENCE: 8

tgactgtgaa cgttcgagat ga                                              22
```

IMMUNOSTIMULATORY COMPOSITIONS, PARTICLES, AND USES RELATED THERETO

CROSS-REFERENCE TO RELATED APPLICATIONS

This application is a continuation of U.S. application Ser. No. 15/833,769 filed Dec. 6, 2017, which is a continuation of U.S. application Ser. No. 14/374,729 filed Jul. 25, 2014, which is the National Stage of International Application No. PCT/US2013/024355 filed Feb. 1, 2013, which claims the benefit of U.S. Provisional Application No. 61/594,754 filed Feb. 3, 2012. The entirety of each of these applications is hereby incorporated by reference for all purposes.

STATEMENT REGARDING FEDERALLY SPONSORED RESEARCH OR DEVELOPMENT

This invention was made with government support under Grant RO1CA138993 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 12011USCON_ST25.txt. The text file is 17 KB, was created on Dec. 6, 2017, and is being submitted electronically via EFS-Web.

BACKGROUND

Provenge™ is a recently FDA-approved autologous cellular immunotherapy treatment. Peripheral blood leukocytes of a subject are harvested via leukapheresis. These enriched monocytes are incubated with prostatic acid phosphatase (PAP) conjugated to cytokine granulocyte macrophage colony stimulating factor (GM-CSF). GM-CSF is thought to direct the target antigen to receptors on DC precursors, which then present PAP on their cell surface in a context sufficient to activate T cells for the cells that express PAP. Activated, PAP presenting DCs are administered to the subject to elicit an immune response retarding cancer growth. This strategy requires isolation and expansion of cells of the subject, and typically treatment does not entirely clear the subject of cancer or tumors. Thus, there is a need to identify improved methods.

B7-1 (also known as CD80) is a T cell costimulatory molecule that can be anchored in to autologous cancer cells to stimulate immune responses. McHugh et al., report the construction, purification and functional reconstitution of a glycolipid anchored form of B7-1 (CD80) on tumor cell membranes. Proc. Natl. Acad. Sci. USA 1995; 92:8059-8063. See also U.S. Pat. No. 6,491,925. Glycosyl phosphatidylinositol anchored B7-1 (GPI-B7-1) molecules have been incorporated onto tumor cells and isolated tumor cell membranes to provide costimulation for allogenic T cell proliferation. See Nagarajan & Selvaraj, Vaccine, 2006, 24(13):2264-74, U.S. Published Patent Application No. US 2007/0243159, Bozeman et al., Front Biosci. 2010; 15:309-320. Bumgarner et al., report surface engineering of microparticles by novel protein transfer for targeted antigen/drug delivery. J Control Release. 2009; 137:90-97.

Cubas et al., report virus-like particle (VLP) lymphatic trafficking and immune response generation after immunization by different routes. J Immunotherapy, 2009, 32(2): 118-128. Kueng et al., report a general strategy for decoration of envelope viruses with functionally active lipid-modified cytokines, J Virology, 2007, 81, 8666-8676.

SUMMARY

In some embodiments, described herein is a method of tumor treatment or tumor vaccination. The method generally comprises applying to a human being in need thereof a tumor therapeutic composition or tumor vaccine defined herein. The tumor therapeutic composition or tumor vaccine can be produced by protein transfer of glycosyl-phosphatidylinositol (GPI)-anchored immunostimulatory or costimulatory molecules.

In one embodiment, the tumor therapeutic composition or tumor vaccine comprises a live tumor cell or tumor cell membranes that is or are modified by protein transfer to express one or more GPI-anchored immunostimulatory or costimulatory molecules. The tumor therapeutic composition or tumor vaccine can be prepared by a method that comprises obtaining one or more GPI-anchored immunostimulatory or costimulatory molecules, and transferring the GPI-anchored immunostimulatory or costimulatory molecules onto a tumor cell or isolated tumor cell membranes by protein transfer.

In certain embodiments, the disclosure relates to non-naturally occurring particle comprising, a lipid membrane; a B7-1 and/or B7-2 molecule anchored to the lipid membrane on the exterior of the particle; and an antigen molecule such as a tumor specific antigen or cancer marker anchored to the lipid membrane on the exterior of the particle. Typically, the particle further comprises an adjuvant molecule anchored to the lipid membrane on the exterior of the particle wherein the adjuvant molecule and antigen molecule are not the same molecule. In certain embodiments, the adjuvant molecule is selected from IL-2, IL-12, ICAM1 GM-CSF, flagellin, unmethylated, CpG oligonucleotide, lipopolysaccharides, lipid A, and heat stable antigen (HSA). The lipid membrane may be a phospholipid monolayer or phospholipid bilayer. Typically, the particle is selected from a cell, allogeneic or autologous cancer cell or its membrane fragments or vesicles, liposome, virosome, micelle, polymer, and virus like particle.

In certain embodiments, the B7-1 molecule is anchored to the lipid membrane on the exterior of the particle through a conjugated glycosyl-phosphatidylinositol, phospholipid, glycolipid, triglyceride, saturated or unsaturated fatty acid, or other lipophilic molecule.

In certain embodiments, the antigen molecule such as a tumor associated antigen or cancer marker is anchored to the lipid membrane on the exterior of the particle through a conjugated glycosyl-phosphatidylinositol, phospholipid, glycolipid, triglyceride, saturated or unsaturated fatty acid, or other lipophilic molecule.

In certain embodiments, the adjuvant molecule is anchored to the lipid membrane on the exterior of the particle through a conjugated glycosyl-phosphatidylinositol, phospholipid, glycolipid, triglyceride, saturated or unsaturated fatty acid, or other lipophilic molecule.

Particles comprising membranes such as tumor membranes carrying tumor antigens and immunostimulatory stimulatory molecules can be modified by incubating with lipophilic adjuvants such as lipopolysaccharides or an immunostimulatory unmethylated CpG oligonucleotides lipid conjugate.

In certain embodiments, antigen is a cancer marker molecule selected from HER-2, MUC-1, mucin antigens TF, Tn, STn, glycolipid globo H antigen, prostate-specific antigen, prostate-specific membrane antigen, early prostate cancer antigen-2 (EPCA-2), BCL-2, MAGE antigens such as CT7, MAGE-A3 and MAGE-A4, G-protein coupled estrogen receptor 1, CA15-3, CA19-9, CA 72-4, CA-125, carcinoembryonic antigen, CD20, CD31, CD34, PTPRC (CD45), CD99, CD117, melanoma-associated antigen (TA-90), peripheral myelin protein 22 (PMP22), epithelial membrane proteins (EMP-1, -2, and -3), HMB-45 antigen, MART-1 (Melan-A), S100A1, S100B and gp100:209-217(210M).

In certain embodiments, the disclosure relates to virus like particles comprising B7-1 and/or B7-2 molecule anchored to a lipid membrane on the exterior of the particle and an antigen molecule anchored to the lipid membrane on the exterior of the particle. Typically, the antigen molecule is a cancer marker or tumor associated antigen or tumor-specific antigen selected from HER-2, MKI67, prostatic acid phosphatase (PAP), prostate-specific antigen (PSA), prostate-specific membrane antigen, early prostate cancer antigen-2 (EPCA-2), BCL-2, MAGE antigens, antigens comprising a Mage Homology Domain (MHD), MAGE-1, CT7, MAGE-A3 and MAGE-A4, ERK5, G-protein coupled estrogen receptor 1, CA15-3, CA19-9, CA 72-4, CA-125, carcinoembryonic antigen, CD20, CD31, CD34, PTPRC (CD45), CD99, CD117, melanoma-associated antigen (TA-90), peripheral myelin protein 22 (PMP22), epithelial membrane proteins (EMP-1, –2, and –3), HMB-45 antigen, MART-1 (Melan-A), S100A1, S100B and gp100:209-217(210M). Typically, the virus like particle further comprising an adjuvant molecule anchored to a lipid membrane on the exterior of the particle wherein the adjuvant molecule and the antigen molecule are not the same molecule. In certain embodiments, the adjuvant molecule is selected from is IL-2, IL-12, ICAM1 GM-CSF, flagellin, unmethylated, CpG oligonucleotide, lipopolysaccharides, lipid A, and heat stable antigen (HSA).

In certain embodiments, the disclosure relates to methods of treating cancer comprising administering an effective amount of a particle or a virus like particle as disclosed herein to a subject at risk of or diagnosed with cancer or a tumor optionally in combination with anti-CTLA-4 antibodies such as abatacept, belatacept, ipilimumab, tremelimumab, anti-PD-1 and PDL1 antibodies such as nivolumab, unmethylated CpG oligonucleotide, methyl jasmonate, cyclophosphamide, gemcitabine or other immunosuppression blocker or other anticancer agent. Typically, the subject is a human subject and the virus like particle comprises a B7-land/or B7-2 molecule anchored to a lipid membrane on the exterior of the particle and an antigen molecule wherein the antigen molecule is a viral protein.

Other anticancer agents contemplated include gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin bortezomib anegrilide, tamoxifen, toremifene, raloxifene, droloxifene, iodoxyfene fulvestrant, bicalutamide, flutamide, nilutamide, cyproterone, goserelin, leuprorelin, buserelin, megestrol anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

In certain embodiments, the viral like particle has an hemagglutinin selected from influenza H1, H2, H3, H4, H5, H6, H7, H8, H9, H10, H11, H12, H13, H14, H15, and H16 optionally in combination with or individually influenza N1, N2, N3, N4, N5, N6, N7, and N8.

In certain embodiments, the virus protein is an HIV envelope protein selected from gp 41, gp 120, and gp 160.

In certain embodiments, the disclosure relates to methods of treating or preventing a viral infection comprising administering an effective amount of a virus like particle disclosed herein to a subject at risk of, exhibiting symptoms of, or diagnosed with a viral infection.

In certain embodiments, the disclosure relates to particles comprising a cancer marker made by the process of mixing a cancer marker conjugated to a lipophilic moiety and a particle comprising a lipid membrane. Typically, the cancer marker is HER-2 or PSA or PAP.

In certain embodiments, the disclosure relates to particles comprising a cancer marker and B7-1 and/or B7-2 made by the process of mixing a B7-1 and/or B7-2 conjugated to a lipophilic moiety and a particle comprising a lipid membrane and a cancer marker.

In certain embodiments, the disclosure relates to methods of treating or preventing breast cancer comprising administering an effective amount of a particle comprising B7-1 and/or B7-2, GM-CSF, and HER-2 to a subject in need thereof.

In certain embodiments, the method further comprises analyzing the subject for overexpression of HER-2, by measuring, detecting, sequencing, hybridizing with a probe, HER-2 polypeptide or a nucleic acid indicative of HER-2 expression, or sequencing a nucleic acid associated with HER-2, on a cancer cell or tumor cell isolated from the subject.

In certain embodiments, the disclosure relates to methods of treating or preventing prostate cancer comprising administering an effective amount of a particle comprising B7-1 and/or B7-2, GM-CSF, and PSA or PAP to a subject in need thereof.

In certain embodiments, the disclosure relates to methods of treating or preventing prostate cancer comprising administering an effective amount of a particle comprising B7-1 and/or B7-2, GM-CSF, IL-12, and PSA or PAP to a subject in need thereof.

In certain embodiments, the compositions and method further comprises administering an immunostimulatory amount of particles disclosed herein in combination with an anticancer agent, individually as single agents and/or in a single pharmaceutical composition.

In the case of breast cancer the anticancer agent may be estradiol, tamoxifen, cetuximab and a HER-2 antibody, humanized antibody, or human chimera such as trastuzumab, pertuzumab. The HER-2 antibodies may be administered before or after immune stimulation with particle.

In the case of prostate cancer, the anticancer agent may be docetaxel, cabazitaxel, bevacizumab, alpharadin thalidomide, prednisone, abiraterone, finasteride and dutasteride, MDV3100, orteronel (TAK-700), omega-3 fatty acids such as ethyl esters of eicosapentaenoic acid (EPA) and/or docosahexaenoic acid (DHA) or combinations thereof such as bevacizumab, docetaxel, thalidomide, and prednisone or abiraterone acetate in combination with prednisone.

In another embodiment, the tumor therapeutic composition or tumor vaccine comprises a microparticle with a lipid membrane encapsulating tumor antigens or peptides and one or more anchored immunostimulatory or costimulatory molecules expressed on the surface of the particle. The tumor therapeutic composition or tumor vaccine can be prepared by a method that comprises obtaining one or more anchored immunostimulatory or costimulatory molecules, and transferring the anchored immunostimulatory or costimulatory molecules onto a particle encapsulating at least one tumor antigen or peptide, tumor lysate, tumor membranes, or combinations thereof by protein transfer.

The microparticles can be formed of any biocompatible polymer capable of incorporating GPI-anchored immunostimulatory or costimulatory molecules. For example, representative useful biocompatible polymers include, but are not limited to, polyvinyl alcohols, polyvinyl ethers, polyamides, polyvinyl esters, polyvinylpyrrolidone, polyglycolides, polyurethanes, allyl celluloses, cellulose esters, hydroxypropyl derivatives of celluloses and cellulose esters, preformed polymers of poly alkyl acrylates, polyethylene, polystyrene, polyactic acid, polyglycolic acid, poly(lactide-co-glycolide), polycaprolactones, polybutyric acids, polyvaleric acid and copolymers thereof, alginates, chitosans, gelatin, albumin, zein and combinations thereof.

Anchored immunostimulatory or costimulatory molecules can be obtained by expressing the GPI-anchored immunostimulatory or costimulatory molecules in a cell, and isolating the GPI-anchored immunostimulatory or costimulatory molecules. The anchored immunostimulatory or costimulatory molecules can be any substance that stimulates or costimulates immune reaction against a tumor cell that is capable of being expressed in a cell. For example, the immunostimulatory or costimulatory molecules useful here can be a cytokine molecule. In one embodiment, a useful cytokine can be, for example, one or more of cytokines IL-2, IL-4, IL-6, IL-12, IL-15, IL-18, IL-19, granulocyte-macrophage colony stimulating factor (GM-CSF), and combinations thereof. In another embodiment, the immunostimulatory or costimulatory molecules can be, for example, the immunostimulatory or costimulatory molecules useful here can be a cytokine molecule. In another embodiment, the immunostimulatory or costimulatory molecules useful here can be, for example, B7-1, B7-2 and an intercellular adhesion molecule such as CD40L, ICAM-1, ICAM-2, and ICAM-3.

In any of the embodiments, particle may be a wild type cell, cancer cell or immortalized cell.

The immunostimulatory or costimulatory molecules can be used alone or together and can be used in conjunction with antibody fusion proteins.

The tumor therapeutic composition or tumor vaccine described herein can be used therapeutically or prophylactically for the treatment or prevention of a tumor. Representative tumors can be treated or prevented include, but are not limited to, breast cancer, prostate cancer, lung cancer, melanoma, liver cancer, leukemia, lymphoma, myeloma, colorectal cancer, gastric cancer, bladder carcinoma, esophageal carcinoma, head & neck squamous-cell carcinoma, sarcomas, kidney cancers, ovarian and uterus cancers, adenocarcinoma, glioma, and plasmacytoma, and combinations thereof.

In one embodiment, the vaccine or therapeutic composition described herein can be GPI-anchored cytokine such as GPI-IL-2 and GPI-IL-12 alone or in combination with GPI-anchored costimulatory molecules such as GPI-B7-1, GPI-B7-2, GPI-ICAM-1, GPI-ICAM-2 and GPI-ICAM-3. Such a vaccine or therapeutic composition can be used for the treatment of tumor and other diseases such as viral, bacterial and parasitic diseases.

In another embodiment, the vaccine and therapeutic composition can be biocompatible microparticles such as biodegradable microparticles modified with GPI-anchored immunostimulatory molecules such as IL-2, IL-4, IL-6, IL-12, ICAM-1, ICAM-2, ICAM-3, B7-1, B7-2, CD40L, IL-15, IL-18, IL-19, granulocyte-macrophage colony stimulating factor (GM-CSF), and combinations thereof.

In yet another embodiment, the vaccine or therapeutic compositions described herein can be tumor cells or membranes modified by protein transfer with GPI-anchored cytokines alone or/and in combination with other cytokines or/and other costimulatory molecules. One such embodiment can be, for example, tumor membranes modified with purified GPI-IL-12.

In a further embodiment, particles like inactivated or partially attenuated virus, bacteria and virus-like particles can be modified to express immunostimulatory molecules by protein transfer with GPI-anchored cytokines and immunostimulatory molecules. Vaccines and therapeutic compositions prepared in this manner can be used for preventing or treating viral, bacterial, or parasitic diseases or disorders.

In some other embodiments, the vaccine and therapeutic compositions described herein can be used for treating autoimmune disorders. For example, membrane anchored cytokines such as IL-10 and TGF-beta can also be used to induce tolerance or to suppress immunity which can be used in treating autoimmune diseases and transplant rejection.

Before the sequence, an optimized IL-2 Kozak sequence along with the restriction enzyme sites HindIII and KpnI have been added. Following the hHER2ECD sequence an EcoRI site is added. At base pair position 1365 of hHER2, a change in base pair from T was made to C in order to remove an EcoRI restriction enzyme site at this position, however, the final amino acid still remains as an isoleucine.

Figure 12:
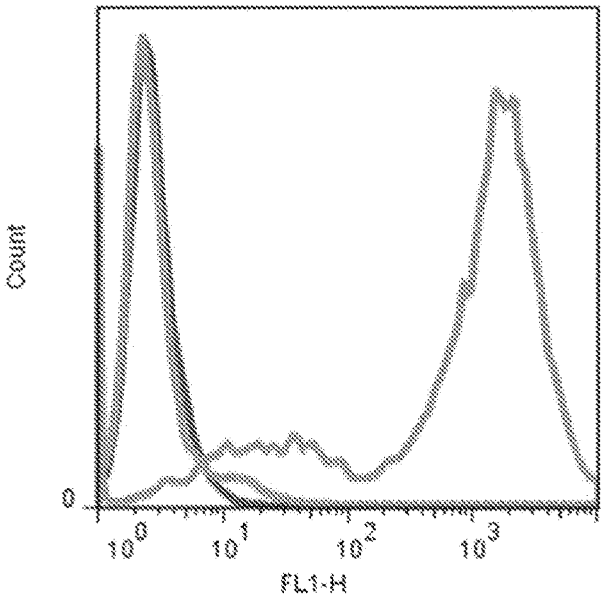

FIG. 12 shows flow cytometry analysis of CHO cells expressing GPI-human HER-2 (hHER-2-CD59) using TA1 mAb.

DETAILED DESCRIPTION

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms “a,” “an,” and “the” include plural referents unless the context clearly dictates otherwise. Thus, for example, reference to “a support” includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, the term “combination with” when used to describe administration with an additional treatment means that the agent may be administered prior to, together with, or after the additional treatment, or a combination thereof.

As used herein, the terms “prevent” and “preventing” include the prevention of the recurrence, spread or onset. It is not intended that the present disclosure be limited to complete prevention. In some embodiments, the onset is delayed, or the severity is reduced.

As used herein, the terms “treat” and “treating” are not limited to the case where the subject (e.g. patient) is cured and the disease is eradicated. Rather, embodiments of the present disclosure also contemplate treatment that merely reduces symptoms, and/or delays disease progression.

“Subject” refers any animal, preferably a human patient, livestock, rodent, monkey or domestic pet.

The terms “protein” and “polypeptide” refer to compounds comprising amino acids joined via peptide bonds and are used interchangeably.

As used herein, an “amino acid sequence” refers to an amino acid sequence of a protein molecule. The terms such as “polypeptide” or “protein” are not meant to limit the amino acid sequence to the deduced amino acid sequence, but such as amino acid deletions, additions, and modifications such as glycolsylations and addition of lipid moieties or other post-translational modifications.

With regard to any of the antigens or adjuvants disclosed herein, the protein generally refers to the most frequent human isoform, variant, mutated form, or protein with substantially identity to the full-length or portion thereof. Typically, an appropriate fragment is of the extracellular domain.

The term “portion” when used in reference to a protein (as in “a portion of a given protein”) refers to fragments of that protein. The fragments may range in size from four amino acid residues or more than twenty or thirty or the entire amino sequence minus one amino acid.

The following terms are used to describe the sequence relationships between two or more proteins: “reference sequence”, “sequence identity”, “percentage of sequence identity”, and “substantial identity”. A “reference sequence” is a defined sequence used as a basis for a sequence comparison; a reference sequence may be a subset of a larger sequence, for example, as a segment of a full-length amino acid sequence of a protein. Generally, a reference sequence is at least 20 amino acids in length, frequently at least 25 amino acids in length, and often at least 50 amino acids in length. Since two proteins may each (1) comprise a sequence (i.e., a portion of the complete amino acid sequence) that is similar between the two protein, and (2) may further comprise a sequence that is divergent between the two proteins, sequence comparisons between two (or more) proteins are typically performed by comparing sequences of the two proteins over a “comparison window” to identify and compare local regions of sequence similarity. A “comparison window”, as used herein, refers to a conceptual segment of at least 20 contiguous nucleotide positions wherein a sequence may be compared to a reference sequence of at least 20 contiguous amino acids and wherein the portion of the sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two sequences are identical (i.e., on a nucleotide-by-nucleotide basis) over the window of comparison. The term "percentage of sequence identity" is calculated by comparing two optimally aligned sequences over the window of comparison, determining the number of positions at which the identical amino acids occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a sequence, wherein the protein comprises a sequence that has at least 85 percent sequence identity, preferably at least 90 to 95 percent sequence identity, more usually at least 99 percent sequence identity as compared to a reference sequence over a comparison window of at least 20 amino acid positions, frequently over a window of at least 25-50 nucleotides, wherein the percentage of sequence identity is calculated by comparing the reference sequence to the sequence which may include deletions or additions which total 20 percent or less of the reference sequence over the window of comparison.

Particle Anchored Immunostimulatory or Costimulatory Molecules

In certain embodiments, the disclosure relates to non-naturally occurring particle comprising, a B7-1 and/or B7-2 molecule anchored on the exterior of the particle; and an antigen molecule such as a tumor specific antigen or cancer marker anchored to the lipid membrane on the exterior of the particle. In certain embodiments, the B7-1 and or B7-2 or antigen, or protein may be anchored onto the membrane of the particle through a variety of linkages, such as lipid palmatic acid, biotin-avidin interaction, or a GPI-anchor.

In one example, a contemplated sequence of B7-1 is mghtrrqgts pskcpylnff qllvlaglsh fcsgvihvtk evkevatlsc ghnvsveelaqtriywqkek kmvltmmsgd mniwpeyknr tifditnnls ivilalrpsd egtyecvvlk yekdafkreh laevtlsvka dfptpsisdf eiptsnirri icstsggfpe phlswlenge elnainttvs qdpetelyav sskldfnmtt nhsfmcliky ghlrvnqtfn wnttkqehfp dnllpswait lisvngifvi ccltycfapr crerrrnerl rresvrpv (SEQ ID NO: 1) or fragment thereof.

In another example, a contemplated sequence is vihvtkevke vatlscghnv sveelaqtri ywqkekkmvl tmmsgdmniw peyknrtifd itnnlsivil alrpsdegty ecvvlkyekd afkrehlaev tlsvkadfpt psisdfeipt snirriicst sggfpephls wlengeelna inttvsqdpe telyaysskl dfnmttnhsf mclikyghlr vnqtfnwntt kqehfpdn (SEQ ID NO:2) or fragment thereof. See Stamper et al., Crystal structure of the b7-1/ctla-4 complex that inhibits human immune responses. Nature (2001) 410:608.

In another example, a contemplated fragment is KAMEIVAQPAV VLASSRGIAS FVCEYASPGK ATEVRVTVLR QADSQVTEVC AATYMMGNELTFLDDSICTG TSSGNQVNLT IQGLRAMDTG LYICKVELMY PPPYYLGIGN GAQIYVIDPE PCPDSD (SEQ ID NO: 3) or fragment thereof.

In certain embodiments, the disclosure relates to non-naturally occurring particle comprising, a B7-1 and/or B7-2 molecule anchored on a lipid membrane; a B7-1 and/or B7-2 molecule anchored to the lipid membrane on the exterior of the particle; and an antigen molecule such as a tumor specific antigen or cancer marker anchored to the lipid membrane on the exterior of the particle.

A number of proteins commonly expressed by cells are attached to the cell membrane via a GPI-anchor. These proteins are post-translationally modified at their carboxy terminus to express this glycosylated moiety which is synthesized in the endoplasmic reticulum. These naturally expressing GPI-anchored molecules are widely distributed in mammalian cells and serve a host of different cellular functions, such as cell adhesion, enzymatic activity, and complement cascade regulation. Naturally occurring GPI-anchored proteins lack a transmembrane and cytoplasmic domain that otherwise anchor membrane proteins. The GPI-anchor consists of a glycosylated moiety attached to phosphatidylinositol containing two fatty acids. The phosphatidylinositol portion, as well as an ethanolamine which is attached to the C-terminal of the extracellular domain of the membrane proteins, anchor the molecule to the cell membrane lipid bilayer.

In order to exploit this natural linkage using recombinant DNA techniques, the transmembrane and cytoplasmic domains of a transmembrane surface protein need only be replaced by the signal sequence for GPI-anchor attachment that is found at the hydrophobic C-terminus of GPI-anchored protein precursors. This method may be used to generate GPI-anchored proteins is not limited to membrane proteins; attaching a GPI-anchor signal sequence to secretory proteins would also convert them to a GPI-anchored form. The method of incorporating the GPI-anchored proteins onto isolated cell surfaces or lipid particles is referred to here as protein transfer.

GPI-anchored molecules can be incorporated onto lipid membranes spontaneously. These GPI-anchored proteins can be purified from one cell type and incorporated onto different cell membranes. GPI-anchored proteins are used to customize of the lipid membranes disclosed herein for uses as a cancer vaccine. One may incorporate multiple molecules simultaneously onto the same cell membrane. One can control the level of protein expression by simply varying the concentration of the GPI-anchored molecules to be incorporated. The most significant outcome of this technology will be the reduction of time in preparing cancer vaccines from months to hours. These features make the protein transfer approach a more viable choice for the development of cancer vaccines for clinical settings. The molecules incorporated by means of protein transfer retain their functions associated with the extracellular domain. Cells and isolated membranes can be modified to express immunostimulatory molecules. In certain embodiments, the disclosure contemplates that the GPI-anchored molecules are incorporated onto the surface of albumin microparticles by this protein transfer method. GPI-anchored proteins attached to the surface of microparticles are used to target and/or enhance the adjuvant activity of microparticles, thereby enhancing the capacity to function as a targeted antigen or drug delivery device for cancer treatment.

The GPI-B7-1 expression (by protein transfer) was stable up to 7 days on isolated membranes at 37° C. and frozen membranes can be used up to 3 years of storage at −80° C. which makes the stability and storage a nonissue. These studies suggest that the membrane vaccines are more suitable to stably express the GPI-anchored molecules than on intact cells, which lose the expression within 24 hr.

This approach for introducing proteins onto membranes provides advantages over other immunotherapies for cancer vaccine development. This approach allows a protein to be added either singularly or in a combinatory manner to the tumor membrane surface. This approach navigates around the necessity to establish tumor cells as is the case for gene transfer. This GPI-mediated approach by protein transfer may be used for the co-stimulatory molecules, B7-land B7-2, GM-CSF, IL-2, and IL-12. With these cytokines being attached to the tumor membrane via a GPI-anchor, it enables them to exert their effector functions locally at the vaccination site without the risk of systemic toxicity.

Virus Like Particles

In certain embodiments, the disclosure relates to virus like particles comprising B7-1 and/or B7-2 molecule anchored to a lipid membrane on the exterior of the particle and an antigen molecule anchored to the lipid membrane on the exterior of the particle for uses disclosed herein.

Figure 1:
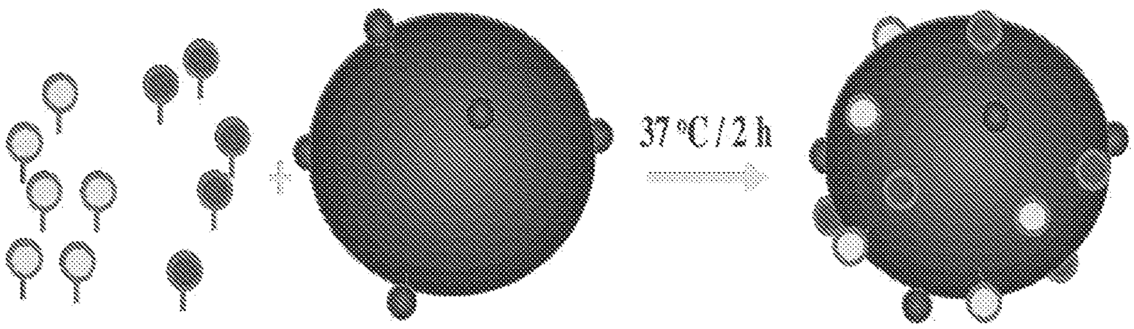
FIG. 1 illustrates the expression tumor associated antigens and immunostimulatory molecules onto particles containing a lipid membrane, e.g., CHO cells and envelope VLPs, using GPI anchoring for protein transfer.

Influenza virus-like particles (VLPs) are particulate in nature and have shown to elicit robust immunity against antigens. Influenza VLPs have an outer lipid bilayer with properties similar to the cell membranes. Modification of influenza VLPs with a protein transfer method to incorporates tumor-associated antigens (TAAs) on the surface along with immunostimulatory molecules (ISMs) elicits enhanced immune responses directed against the TAAs. One contemplated protein transfer approach utilizes glycosyl phosphatidylinositol (GPI)- to anchor the TAA, which can spontaneously incorporate onto the surface of the VLPs that contain a lipid bilayer upon incubation at 37° C. (See FIG. 1).

Incorporation of GPI-anchored forms of TAAs onto the surface of VLPs is used to direct the immune response against cancerous cells whereas the incorporation of immunostimulatory molecules (ISMs), such as GPI-anchored cytokines, costimulatory molecules, and adhesion molecules, onto the surface of VLPs is used to enhance the interaction between VLPs and antigen presenting cells (APCs) as well as lead to activation of these APCs and other immune effector cells. The incorporation of GPI-TAAs and GPI-ISMs onto VLPs by protein transfer leads to an anti-tumor immune response and tumor regression.

VLPs consist of a virus' capsid protein shell that presents viral antigens in an authentic conformation without the viral genome that is required for replication. Thus, they provide a safe approach for human use. VLPs contain a multivalent repetitive structure that is particulate in nature, allowing for recognition by many pattern recognition receptors and the induction of an enhanced innate and adaptive immune response. The particulate nature of VLPs allows for them to be readily taken up and presented by APCs, and thus could provide a means for breaking the immunosuppressive barrier initiated by the tumor microenvironment.

In certain embodiments, influenza virus-like particles (VLPs) may be produced using a variety of platform systems, including recombinant baculovirus vectors, transient plasmid expression systems, stable cell-line transformants, and plant expression systems. Typically VLPs are non-replicating particles that spontaneously self-assemble from expressed influenza virus proteins. In some expression systems, the viral hemagglutinin (HA) protein is sufficient for particle assembly and release from the cell. Typically the VLP comprises neuraminidase (NA). HA may present with a different type of glycosylation depending on whether they are obtained from. For the production of VLPs containing HA in mammalian cells, co-expression of NA or exogenously added NA was required for the effective release of influenza VLPs into culture media, implying an important role of the NA activity in cleaving sialic acids bound to HA of budding particles. In contrast, VLPs containing HA can be produced in insect cells in the absence of NA expression. Insect cells do not add sialic acids to the N-glycans during the posttranslational modification, which explains how VLPs containing HA but not NA are effectively released from insect cell surfaces. See Kang et al., Virus Res. 2009c, 143 (2), 140-6.

In certain embodiments, VLPs used herein are recombinant influenza VLPs that have been generated in insect cells infected with rBVs expressing influenza genes HA, NA, M1, and M2.

In certain embodiments, VLPs used herein are recombinant influenza VLPs that have been generated in insect cells infected with rBVs expressing influenza genes HA, NA, and M1.

In certain embodiments, VLPs used herein are recombinant influenza VLPs that have been generated in insect cells infected with rBVs expressing influenza genes of HA and M1.

In some instances, the VLP is obtained from influenza VLPs expressed from recombinant baculovirus (rBV) produced by replication in an insect cell system, e.g., Spodoptera frugiperda SF9 cells.

In some instances, the VLP is obtained from a modified vaccinia virus Ankara (MVA) system expressing influenza H5N1 HA, NA, and M proteins to generate influenza VLPs produced by replication in mammalian cells. See Schmeisser et al., Vaccine, 2012, 30(23):3413-3422.

Tumor Associate Antigens and Cancer Markers

In certain embodiments, the disclosure relates to particles such as cells or virus like particles comprising B7-1 and/or B7-2 molecule anchored to a lipid membrane on the exterior of the particle and an antigen molecule anchored to the lipid membrane on the exterior of the particle. Typically, the antigen molecule is a cancer marker selected from HER-2, MKI67, prostatic acid phosphatase (PAP), prostate-specific antigen (PSA), prostate-specific membrane antigen, early prostate cancer antigen, early prostate cancer antigen-2 (EPCA-2), BCL-2, MAGE antigens such as CT7, MAGE-A3 and MAGE-A4, ERK5, G-protein coupled estrogen receptor 1, CA15-3, CA19-9, CA 72-4, CA-125, carcinoembryonic antigen, CD20, CD31, CD34, PTPRC (CD45), CD99, CD117, melanoma-associated antigen (TA-90), peripheral myelin protein 22 (PMP22), epithelial membrane proteins (EMP-1, -2, and -3), HMB-45 antigen, MART-1 (Melan-A), S100A1, S100B and gp100:209-217(210M), MUC-1, mucin antigens TF, Tn, STn, glycolipid globo H antigen. Typically, the antigen is the human form.

HER-2, or Human Epidermal Growth Factor Receptor 2, refers to the human protein encoded by the ERBB2 gene that has been referred to as Neu, ErbB-2, CD340 (cluster of differentiation 340) or p185. See Coussens et al., 1985, Science 230 (4730): 1132-9.

In certain embodiments, HER-2 is the extracellular domain or fragment thereof. In one contemplated example the protein comprises or consists essentially of the following sequence: TQVCTGTDMK LRLPASPETH LDMLRH-LYQG CQVVQGNLEL TYLPTNASLS FLQDIQEVQG YVLIAHNQVR QVPLQRLRIV RGTQLFEDNY ALA-VLDNGDP LNNTTPVTGA SPGGLRELQL RSLTEILKGG VLIQRNPQLC YQDTILWKDI FHKNNQLALT LIDTNRSRAC HPCSPMCKGS RCW-GESSEDC QSLTRTVCAG GCARCKGPLP TDC-CHEQCAA GCTGPKHSDC LACLHFNHSG ICELHCPALV TYNTDTFESM PNPEGRYTFG ASCVTACPYN YLSTDVGSCT LVCPLHN QEVTAE-DGTQRCE KCSKPCARVC YGLGMEHLRE VRAVT-SANIQ EFAGCKKIFG SLAFLPESFD GDPASNTAPL QPEQLQVFET LEEITGYLYI SAWPDSLPDL SVFQNLQVIR GRILHNGAYS LTLQGLGISW LGLRSL-RELG SGLALIHHNT HLCFVHTVPW DQLFRNPHQA LLHTANRPED ECVGEGLACH QLCARGHCWG PGPTQCVNCS QFLRGQECVE ECRVLQGLPR EYVNARHCLP CHPECQPQNG SVTCFGPEAD QCVACAHYKD PPFCVARCPS GVKPDLSYMP IWKFPDEEGA CQPCPIN (SEQ ID NO: 4) or fragment thereof.

In one contemplated example, the protein comprises or consists essentially of the following sequence: diqmtqspss lsasvgdrvt itcrasqdvn tavawyqqkp gkapklliys asflysgvps rfsgsrsgtd ftltisslqp edfatyycqq hyttpptfgq gtkveikrtv aapsvfifpp sdeqlksgta svvcllnnfy preakvqwkv dnalqsgnsq esvteqdskd styslsstlt lskadyekhk vyacevthqg lsspvtksfn rgec (SEQ ID NO: 5) or fragment thereof.

In one contemplated example, the protein comprises or consists essentially of the following sequence: GTSHLVK-CAE KEKTFCVNGG ECFMVKDLSN PSRYLCKCPN EFTGDRCQNY VMASF (SEQ ID NO: 6) or fragment thereof.

MKI67, or antigen identified by monoclonal antibody Ki-67, refers to the human protein that is encoded by the MKI67 gene. See Bullwinkel et al., 2006, J. Cell. Physiol. 206 (3): 624-35.

PAP, or Prostatic acid phosphatase or prostatic specific acid phosphatase (PSAP), refers to the human enzyme produced by the prostate in males. See Ostrowski & Kuciel, 1994, Clin. Chim. Acta 226 (2): 121-9.

PSA, or Prostate-specific antigen or gamma-seminoprotein or kallikrein-3 (KLK3), refers to the human protein encoded by the KLK3 gene. See Menez et al., J Mol Biol. 2008, 376(4):1021-33.

PSMA, or Prostate-specific membrane antigen or Glutamate carboxypeptidase II, refers to a human type 2 integral membrane glycoprotein found in prostate tissues. See William et al., Reviews on Recent Clinical Trials, 2007, 2, 182-190.

Bcl-2, or B-cell lymphoma 2 refers to an protein encoded by the BCL2 gene. Bcl-2 has two isoforms that differ by two amino acids. Isoform 1 is known as 1G5M, and Isoform 2 is known as 1G5O/1GJH. See Petros et al., 2001, PNAS, 98: 3012-3017. Both isoforms are contemplated antigens.

In certain embodiments, the antigen is the entire protein, polypeptide, or a substantial fragment, or a fragment with conserved substitutions. The fragment may contain 5, 10, 20, 50, 100, or halve of the amino acids in the full length antigen. The fragment may be sufficient to mimic or replicate the folding of the full length antigen. The conserved substitutions may be amino acids that are in the interior of the folded polypeptide. A fragment is sufficient produce antibody production to the polypeptide. The antigen may be a chimera containing the fragment. The antigen may contain 1, 2, or 3, or 5 to 10, or 10 to 20 or more conserved substitutions within the full length or polypeptide fragment which are typically outside of functional domains. In certain embodiments, the antigen may have 80%, 90%, 95% or greater sequence identity to the full length or polypeptide fragment. An antigen protein may or may not be glycosylated.

Adjuvant Molecules

In certain embodiments, the virus like particles disclosed herein comprise an adjuvant molecule anchored to a lipid membrane on the exterior of the particle wherein the adjuvant molecule and the antigen molecule are not the same molecule. In certain embodiments, the adjuvant molecule is selected from is IL-2, IL-12, ICAM1, GM-CSF, flagellin, unmethylated, CpG oligonucleotide, lipopolysaccharides, lipid A, and heat stable antigen (HSA).

It is contemplated that the co-stimulatory molecules, antigens, and adjuvant molecules may the individually conjugated to the lipophilic molecules or two or more or all of them may be conjugated together in a chimera and conjugated to a lipophilic molecule. For example, B7-1 may be conjugated to the adjuvant, HSA, in a chimera and the chimera is conjugated to a GPI.

One contemplated antigen is heat stable antigen (HSA). A hybrid B7-1-HSA molecule on the cell surface membrane can function as a co-stimulatory molecule to induce T cell proliferation. CHO cells and CHO transfectants expressing HSA, B7-1, and B7-1-HSA were used as stimulator cells in a T cell proliferation assay. See Wang et al., Immunology Letters, 2006, 105(2):185-192.

Contemplated TLR 9 ligands as adjuvants are contemplated such as immunostimmulatory unmethylated CpG oligonucleotides, the cytosine of the oligonucleotide sequence 5'-CG-3' is unmethylated and the oligonucleotide is greater than about 6 base pairs in length and is less than about 100 base pairs in length such as 5'-TGACTGT-GAACGTTC GAGATGA-3' (SEQ ID NO:8). It is contemplated that lipophilic molecules may be conjugated to the oligonucleotide for incorporation to the exterior of particles disclosed herein.

In certain embodiments, the antigen is also contained in the interior of the particle.

In certain embodiments, the B7-1 molecule is a B7-1 and heat stable antigen (HSA) hybrid chimera.

In certain embodiments, the antigen is HER-2 and the adjuvant is flagellin and/or GM-CSF.

In certain embodiments, the antigen is HER-2 and the B7-1 molecule is a B7-1 and heat stable antigen (HSA) hybrid chimera.

In certain embodiments, the antigen is HER-2, the adjuvant is flagellin and/or GM-CSF, the B7-1 molecule is a B7-1 and heat stable antigen (HSA) hybrid chimera.

In certain embodiments, the antigen is HER-2 and the adjuvant is IL-12.

In certain embodiments, the antigen is HER-2, the adjuvant is IL-12, the B7-1 molecule is a B7-1 and heat stable antigen (HSA) hybrid chimera.

In certain embodiments, the antigen is PSA or PAP and the adjuvant is flagellin and/or or GM-CSF.

In certain embodiments, the antigen is PSA or PAP and the B7-1 molecule is a B7-1 and heat stable antigen (HSA) hybrid chimera.

In certain embodiments, the antigen is PSA or PAP, the adjuvant is flagellin, the B7-1 molecule is a B7-1 and heat stable antigen (HSA) hybrid chimera.

In certain embodiments, the antigen is PSA or PAP and the adjuvant is IL-12.

In certain embodiments, the antigen is PSA or PAP, the adjuvant is IL-12, the B7-1 molecule is a B7-1 and heat stable antigen (HSA) hybrid chimera.

In certain embodiments, the B7-1 molecule is a B7-1 and heat stable antigen (HSA) hybrid chimera.

In certain embodiments, the antigen is HER-2 and the adjuvant is flagellin and/or GM-CSF.

In certain embodiments, the antigen is HER-2 and the B7-1 molecule is a B7-1 and heat stable antigen (HSA) hybrid chimera.

In certain embodiments, the antigen is HER-2, the adjuvant is flagellin and/or GM-CSF, the B7-1 molecule is a B7-1 and heat stable antigen (HSA) hybrid chimera.

In certain embodiments, the antigen is HER-2 and the adjuvant is IL-12.

In certain embodiments, the antigen is HER-2, the adjuvant is IL-12, the B7-1 molecule is a B7-1 and heat stable antigen (HSA) hybrid chimera.

In certain embodiments, the antigen is PSA or PAP and the adjuvant is flagellin and/or GM-CSF.

In certain embodiments, the antigen is PSA or PAP and the B7-1 molecule is a B7-1 and heat stable antigen (HSA) hybrid chimera.

In certain embodiments, the antigen is PSA or PAP, the adjuvant is flagellin or GM-CSF, the B7-1 molecule is a B7-1 and heat stable antigen (HSA) hybrid chimera.

Cellular Particles

In any of the embodiments, particle may be a wild type cell, cancer cell or immortalized cell.

In certain embodiments, the particle is a cell such as ZR-75-1, ZR-75-30, 184A1, UACC-812, UACC-893, HCC38, HCC70, HCC202, HCC1187, HCC1395, HCC 1428, HCC1500, HCC1569, HCC1599, HCC1806, HCC1937, HCC1954, HCC2157, HCC1419, HCC2218, AU-565, 184B5, MCF 10A, MCF 10F, MCF-12A, BT-20, MDA-kb2, BT-474, CAMA-1, MCF7, MDA-MB-134-VI, MDA-MB-157, MDA-MB-175-VII, MDA-MB-231, MDA-MB-361, SK-BR-3, BT-483, BT-549, DU4475, Hs 578T, MDA-MB-415, MDA-MB-436, MDA-MB-453, MDA-MB-468, T-47D, EFM19, EFM192A, Hs 578Bst, SUM44PE, SUM52PE, SUM102PT, SUM149PT, SUM190PT, 4T1 (CRL-2539), or CAL51 for use in the treatment of cancer, breast cancer, breast adenocarcinoma, or breast carcinoma.

In certain embodiments, the particle is a cell such as Jurkat, Clone E6-1 (ATCC Number: TIB-152), RBL-2H3 (CRL-2256), MOLT-4 (CRL-1582), K-562 (CCL-243), CCRF-CEM (CCL-119), HL-60 (CCL-240), or KG-1 (CCL-246) for use in the treatment of cancer, leukemia, leukemia (AML), leukemia (CIVIL), promyelocytic leukemia, basophilic leukemia, or acute T cell leukemia.

In certain embodiments, the particle is a cell such as NCI-H358 (CRL-5807), LL/2 (CRL-1642), Calu-3 (HTB-55), NCI-H441 (HTB-174), NCI-H1975 (CRL-5908), NCI-H23 (CRL-5800), NCI-H1299 (CRL-5803), NCI-H460 (HTB-177), NCI-H292 (CRL-1848), A-549 (CCL-185), A-549 (CCL-185), A-549 (CCL-185), IMR-90 (CCL-186), MRC-5 (CCL-171), or WI-38 (CCL-75) for use in the treatment of cancer, lung cancer, lung adenocarcinoma, lung carcinoma, lewis lung carcinoma, or bronchioalveolar lung cancer.

In certain embodiments, the particle is a cell such as Ramos (CRL-1596), Daudi (CCL-213), Raji (CCL-86), EL4 (TIB-39), or U-937 (CRL-1593.2) for use in the treatment of cancer, lymphoma, B-cell lymphomas, histiocytic lymphoma, or Burkitt's lymphoma.

In certain embodiments, the particle is a cell such as HeLa (CCL-2) or HeLa S3 (CCL-2.2) for use in the treatment of cancer, cervical cancer or cervical adenocarcinoma.

In certain embodiments, the particle is a cell such as COLO 205 (CCL-222), SW620 (CCL-227), SW480 (CCL-228), LoVo (CCL-229), LS 174T (CL-188), Caco-2 (HTB-37), HT-29 (HTB-38), DLD-1 (CCL-221), HCT 116 (CCL-247), T84 (CCL-248), CT26.WT (CRL-2638) for use in the treatment of cancer, colon cancer, colon carcinoma, or a colon adenocarcinoma.

In certain embodiments, the particle is a cell such as HCN-1A (CRL-10442), U-87 MG (HTB-14), C6 (CCL-107), bEnd.3 (CRL-2299), or T98G (CRL-1690) for use in the treatment of cancer, brain cancer, glioma, glioblastoma multiforme, glioblastoma-astrocytoma, or brain endothelioma cancer.

In certain embodiments, the particle is a cell such as 3197-3 (CRL-1568), 3T3-Swiss albino (CCL-92), BALB/3T3 clone A31 (CCL-163), NTERA-2 cl.D1 (CRL-1973), 3T3-L1 (CL-173), NIH/3T3 (CRL-1658), SK-OV-3 (HTB-77), CHO-K1 (CCL-61), or F-12K (30-2004) for use in the treatment of cancer, ovarian cancer, ovarian adenocarcinoma, or testicular cancer.

In certain embodiments, the particle is a cell such as 293T/17 (CRL-11268), 293 (CRL-1573), VERO C1008 (CRL-1568), Vero (CCL-81), MDCK (CCL-34), BHK-21 (CCL-10), Caki-1 (HTB-46), 786-0 (CRL-1932), or COS-7 (CRL-1651) for use in the treatment of cancer, renal cancer, or renal carcinoma.

In certain embodiments, the particle is a cell such as H9c2 (CRL-1446) for use in the treatment of cancer or cardiac tumors.

In certain embodiments, the particle is a cell such as A-431 (CRL-1555), Detroit 551 (CCL-110), BJ (CRL-2522), B16-F10 (CRL-6475), SK-MEL-28 (HTB-72), A375 (CRL-1619), NCTC clone 929 (CCL-1), IRR-MRC-5 (55-X), or IRR-STO (56-X) for use in the treatment of cancer, skin cancer, squamous-cell carcinoma, melanoma, areolar lesions, or epidermoid carcinoma.

In certain embodiments, the particle is a cell such as HT-1080 (CCL-121) for use in the treatment of cancer or fibrosarcoma.

In certain embodiments, the particle is a cell such as AGS (CRL-1739) or NCI-N87 (CRL-5822) for use in the treatment of cancer, stomach cancer, gastric carcinoma or gastric adenocarcinoma.

In certain embodiments, the particle is a cell such as HepG2/C3A (CRL-10741), Hep 3B2.1-7 (HB-8064), Hep G2 (HB-8065), or Hepa 1-6 (CRL-1830) for use in the treatment of cancer, liver cancer, heptoma, or hepatocellular carcinoma.

In certain embodiments, the particle is a cell such as U266B1 (TIB-196) for use in the treatment of cancer or multiple myeloma.

In certain embodiments, the particle is a cell such as IMR-32 (CCL-127), Neuro-2a (CCL-131), or SK-N-SH (HTB-11) for use in the treatment of cancer or neuroblastoma.

In certain embodiments, the particle is a cell such as Saos-2 (HTB-85), U-2 OS (HTB-96), or MG-63 (CRL-1427) for use in the treatment of cancer, bone cancer, or osteosarcoma.

In certain embodiments, the particle is a cell such as Beta-TC-6 (CRL-11506), AsPC-1 (CRL-1682), BxPC-3 (CRL-1687), MIA PaCa-2 (CRL-1420), PANC-1 (CRL-1469), Capan-1 (HTB-79), or AR42J (CRL-1492) for use in the treatment of cancer, pancreatic cancer, or pancreatic carcinoma.

In certain embodiments, the particle is a cell such as PC-12 (CRL-1721) for use in the treatment of cancer or pheochromocytoma.

In certain embodiments, the particle is a cell such as RPMI 8226 (CCL-155) for use in the treatment of cancer or plasmacytoma.

In certain embodiments, the particle is a cell such as PC-3 (CRL-1435), VCaP (CRL-2876), DU 145 (HTB-81), LNCaP clone FGC (CRL-1740), or 22Rv1 (CRL-2505) for use in the treatment of cancer, prostate cancer, prostate adenocarcinoma.

In certain embodiments, the particle is a cell such as ARPE-19 (CRL-2302) for use in the treatment of cancer, eye cancer, or retinal cancer.

In certain embodiments, the particle is a cell such as RD (CCL-136) for use in the treatment of cancer, sarcoma, or rhabdomyosarcoma.

In certain embodiments, the particle is a cell such as a stem cells, mesenchymal stromal/stem, pluripotent stem cell, embryo, myoblast, hybridoma or macrophage, examples include RAW 264.7 (TIB-71), J774A.1 (TIB-67), C2C12 (CRL-1772), L6 (CRL-1458), Sp2/0-Ag14 (CRL-1581) for use in the treatment of cancer.

Combination Strategies for Cancer Treatment:

In some embodiments, In certain embodiments, the disclosure contemplates compositions disclosed herein and using any of the compositions in combination with the administration of dendritic cell (DC)-based cancer vaccines, systemic administration of cytokines, targeted therapy using Abs or other anti-cancer agents.

In certain embodiments, the disclosure contemplates compositions disclosed herein and using any of the compositions in combination with the administration of dendritic cell (DC)-based cancer vaccines. DCs have the unique ability to take up and process antigens, move into secondary lymphoid tissues, and activate both helper and cytotoxic T cells. Preparation of DC-based cancer vaccines involves loading DCs with known tumor-specific antigens, antigenic peptides, cDNA, or RNA isolated from tumor cells. In certain embodiments, an object of this disclosure is to develop more effective methods to deliver tumor antigens to DCs. One strategy is making hybrid cells by fusing tumor cells, tumor antigens, or conjugates with DCs and using the hybrid cells as vaccines. Combination therapies with DC-based cancer vaccines may be used to treat melanoma, breast cancer, multiple myeloma, NHL, lymphatic leukemia, prostatic adenocarcinoma, lung cancer, and hepatocarcinoma In certain embodiments, the disclosure contemplates compositions disclosed herein and using any of the compositions in combination with antigen activated DCs for cancer treatments. In one example, the compositions are used in combination with DCs fused with granulocyte macrophage colony-stimulating factor (GM-CSF) and prostatic acid phosphatase (PAP) conjugate for cancer treatments.

Provenge, an autologous DC-based vaccine, was approved by the FDA for the treatment of men with advanced prostate cancer. Provenge consists of patient-derived DCs pulsed ex vivo with a recombinant fusion protein (PA 2024) containing granulocyte macrophage colony-stimulating factor (GM-CSF) and prostatic acid phosphatase (PAP), an antigen found in 90-95% of prostate cancers.

Another cell-based approach involves using irradiated whole tumor cells as potential cancer vaccines. This strategy allows the induction of a more polyclonal immune response through the presentation of a wide array of tumor antigens. In certain embodiments, the disclosure contemplates compositions disclosed herein and using any of the compositions in combination with irradiated tumor cells for cancer treatments.

The presence of immunosuppressive cytokines in the tumor microenvironment is an important factor in the establishment of tumors. Through the secretion of immunosuppressive cytokines, such as TGF-β and IL-10, the innate and adaptive immune responses are inhibited during tumor development. In order to overcome this immunosuppression, the systemic administration of certain immunostimulatory cytokines, such as IL-2, IL-12, and IFN-α, has been used to alter the tumor microenvironment to mediate tumor recognition by immune cells. In certain embodiments, the disclosure contemplates compositions disclosed herein and using any of the compositions in combination with cytokines such as IL-2, IL-12, and INF-α for cancer treatments.

Cytokines activate immune cells, such as NK and CD8+ T cells, and can also inhibit tumor angiogenesis. In certain embodiments, the disclosure contemplates compositions disclosed herein and using any of the compositions in combination with IL-2, IL-12, and INF-α for the treatment of metastatic melanoma and renal cell carcinoma (RCC).

T-cell growth cytokine, IL-15, promotes the activation of a variety of immune cells, namely NK, NKT, and memory CD8+ T cells, and can overcome activation-induced cell death (AICD) caused by IL-2. In certain embodiments, the disclosure contemplates compositions disclosed herein and using any of the compositions in combination with IL-15 as a potential cancer immunotherapeutic agent.

In certain embodiments, the disclosure contemplates compositions disclosed herein and using any of the compositions in combination intra-tumoral administration of cytokines, modification of tumor cells to secrete cytokines, and fusion of cytokines with antibodies for cancer treatments. In one embodiment, the cytokine is TNF-α. In one embodiment the cancer is melanoma.

In certain embodiments, the disclosure contemplates compositions disclosed herein and using any of the compositions in combination with administration of soluble GM-CSF and optionally a cytokine for cancer treatments.

In certain embodiments, the disclosure contemplates compositions disclosed herein and using any of the compositions in combination with an antibody therapy for cancer treatment. In certain embodiments, the contemplated anti-bodies are directed to epidermal growth factor receptor (EGFR), human EGFR-2 (HER-2), CD20 (an unglycosylated transmembrane phosphoprotein expressed on B and T cells), CD33 (a transmembrane protein expressed on cells of myeloid lineage and also on some lymphoid cells), CD52 (a highly glycosylated 12 amino acid membrane-anchored glycosylphosphatidylinositol (GPI) protein which is expressed on all circulating lymphocytes), and VEGF. In certain embodiments the antibody may be humanized, chimeric, a radiolabeled mouse antibody for targeted radiation.

In certain embodiments, the disclosure contemplates compositions disclosed herein and using any of the compositions in combination with rituximab for the treatment of B-cell non-Hodgkin's lymphoma or chronic lymphocytic leukemia.

In certain embodiments, the disclosure contemplates compositions disclosed herein and using any of the compositions in combination with ofatumumab for the treatment of B-cell non-Hodgkin's lymphoma or chronic lymphocytic leukemia.

In certain embodiments, the disclosure contemplates compositions disclosed herein and using any of the compositions in combination with ibritumomab (tiuxetan) for the treatment of B-cell non-Hodgkin's lymphoma.

In certain embodiments, the disclosure contemplates compositions disclosed herein and using any of the compositions in combination with tositumomab for the treatment of B-cell non-Hodgkin's lymphoma.

In certain embodiments, the disclosure contemplates compositions disclosed herein and using any of the compositions in combination with gemtuzumab ozogamicin for the treatment of acute myeloid leukemia.

In certain embodiments, the disclosure contemplates compositions disclosed herein and using any of the compositions in combination with alemtuzumab for the treatment of B-cell non-Hodgkin's lymphoma or chronic lymphocytic leukemia.

In certain embodiments, the disclosure contemplates compositions disclosed herein and using any of the compositions in combination with trastuzumab for the treatment of breast cancer.

In certain embodiments, the disclosure contemplates compositions disclosed herein and using any of the compositions in combination with bevacizumab for the treatment of breast, lung, or colon cancer.

In certain embodiments, the disclosure contemplates compositions disclosed herein and using any of the compositions in combination with cetuximab for the treatment of brain and neck, or colon cancer.

In certain embodiments, the disclosure contemplates compositions disclosed herein and using any of the compositions in combination with panitumomab for the treatment of colon cancer.

In certain embodiments, the disclosure relates to methods of treating cancer comprising administering an effective amount of a particle as disclosed herein to a subject at risk of or diagnosed with cancer or a tumor optionally in combination with another anticancer agent. Other anticancer agents contemplated include gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin bortezomib anegrilide, tamoxifen, toremifene, raloxifene, droloxifene, iodoxyfene fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

EXAMPLES

Construct, Express and purify GPI-TAAs

HER-2/neu, a surface glycoprotein, is overexpressed on many aggressive forms of breast cancer. One constructs a GPI-HER-2 by attaching extracellular domain of human HER-2 with a GPI-signal sequence and expresses it on CHOK1 cells by gene transfection. One grows CHO cells, lyses, and purifies GPI-HER-2 by affinity chromatography.

One constructs a pCDNA3.1 plasmid expression vector containing the DNA encoding the GPI-anchored form of human HER-2 attached with the GPI-anchor signal sequence from CD59 to the extracellular domain of HER-2 using PCR and ligation into the vector as described for making GPI-GM-CSF. See Poloso et al., Mol Immunol 38:803-816. One transfects CHOK1 cells with the plasmids encoding GPI-HER-2 and confirms the GPI-anchoring by PI-PLC treatment. One grows cells using roller bottles and lyses the collected cell pellets using the detergent octyl glucoside.

Figure 2:
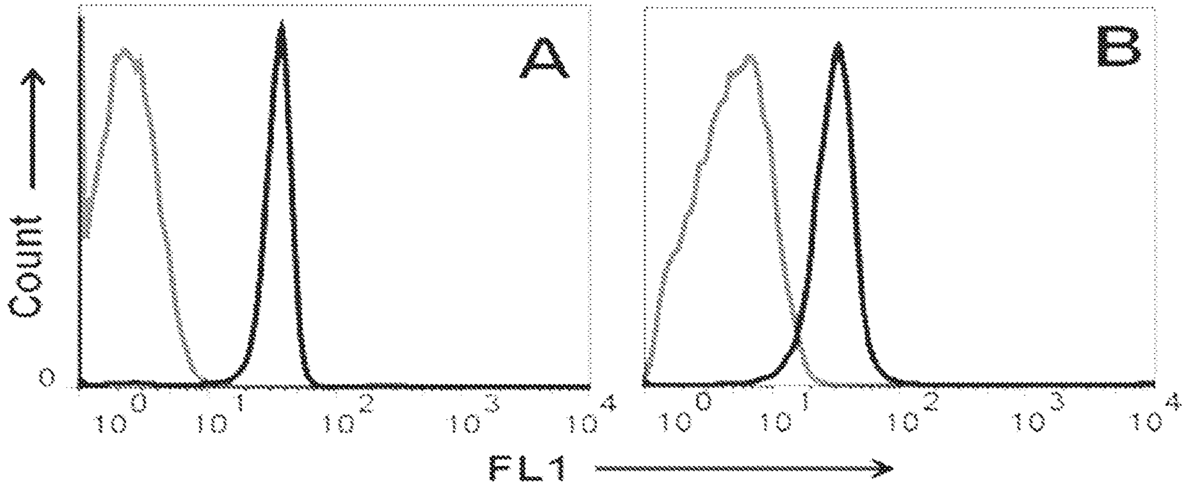
FIG. 2 shows data on protein transfer of (A) GPI-ICAM1 or (B) GPI-IL-12 onto sheep RBCs. Background control; Black: Protein transfer of GPI-ISMs.

Purification and Incorporation of GPI-ICAM1, -IL-12, and –GM-CSF from CHOKI Transfectants CHOK1 cells were transfected to express GPI-ICAM1 or GPI-IL-12. Expression of the GPI-ISMs was assessed by flow cytometry and verification of the GPI-anchor was confirmed by a phospholipase (PIPLC) treatment. The transfectants were grown in large quantities, lysed, and the GPI-ISMs were purified by affinity chromatography. To determine if the purified GPI-ISMs still retained the GPI-anchor and could incorporate onto lipid bilayers by protein transfer, sheep red blood cells (RBCs) were used. The GPI-ISMs were individually incubated with the RBCs at 37° C. for 2 hours, washed and then analyzed by flow cytometry. FIG. 2 demonstrates that the purified GPI-ISMs were able to incorporate onto sheep RBCs.

Optimization of Incorporation of GPI-ISMs onto Influenza H5 VLPs using Protein Transfer These VLPs are constructed by the rBV system through the expression of the hemagluttinin and matrix 1 protein in Sf9 insect cells. See Song et al., J Proteome Res. 2011, 10(8):3450-9.

Figure 3:
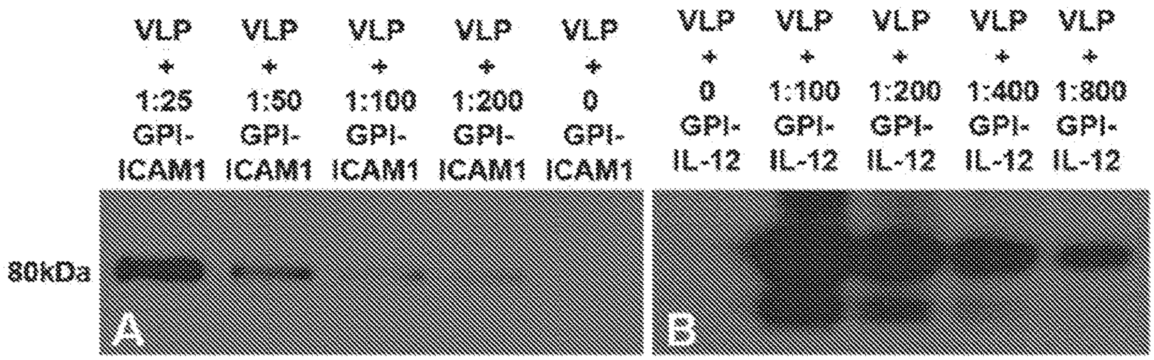
FIG. 3 shows data on Concentration dependent protein transfer of (A) GPI-ICAM-1 or (B) GPI-IL-12 onto H5-VLPs.
Figure 4:
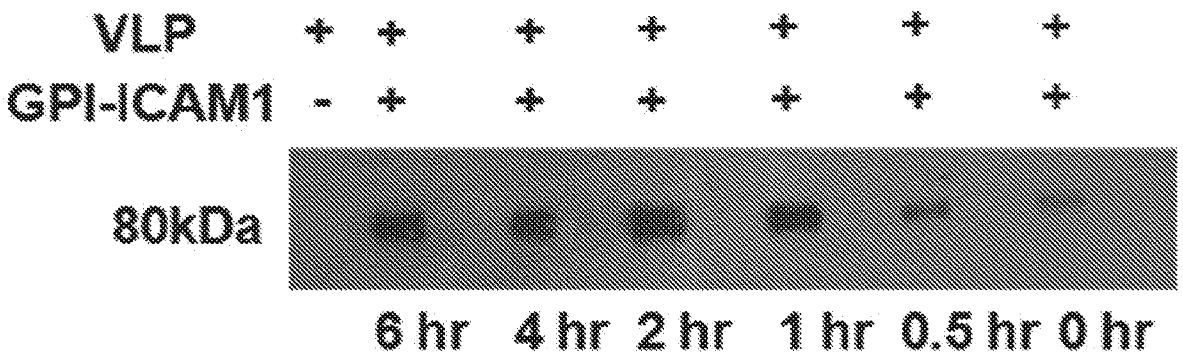
FIG. 4 shows data on the kinetics of protein transfer of GPI-ICAM-1 onto H5 influenza VLPs.

To determine the optimal conditions for incorporation of GPI-ISMs onto influenza H5 VLPs, protein transfer was conducted at different concentrations of GPI-ISMs and at different temperatures. As the concentration of GPI-ISMs was increased, the amount of incorporation, as detected by western blot, also increased (FIG. 3). Optimal incorporation occurred at 37° C. Blotting against the H5 VLPs by using serum from mice injected with H5 VLPs showed that the VLP protein expression was not altered by incorporation of the ISMs. The kinetics of GPI ICAM1 incorporation was also determined to show that maximum incorporation occurs after only 2 hrs of incubation (FIG. 4).

Incorporation of GPI-ISMs onto 115 VLPs by Protein Transfer is GPI-Anchor Dependent.

Figure 5:
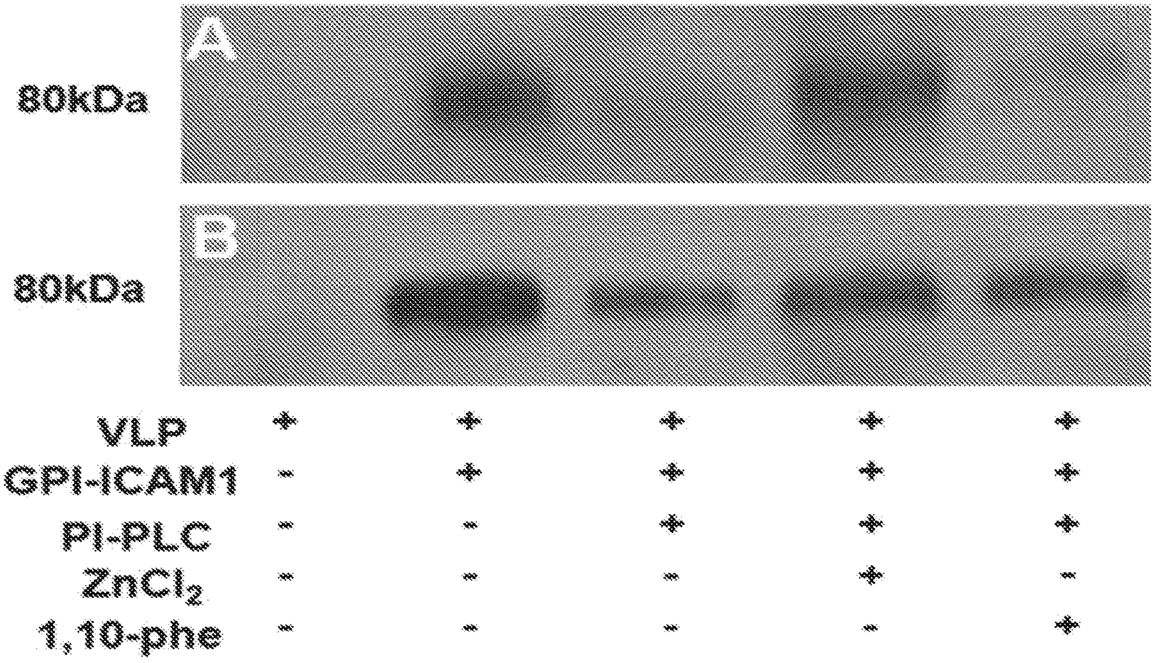
FIG. 5 shows data on the specificity of protein transfer of GPI-ICAM1 onto VLPs.
Figure 6:
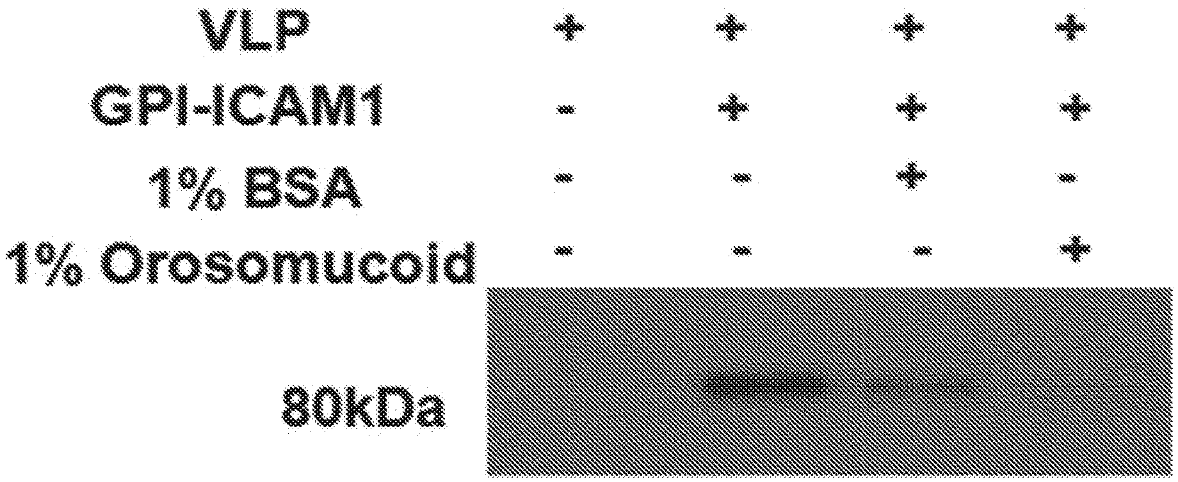
FIG. 6 shows data on the inhibition of protein transfer of GPI-ICAM1 via fatty acid binding proteins.

To determine if incorporation of GPI-ISMs onto VLPs occurred via the GPI-anchor or via non-specific binding, PI-PLC treatment to cleave the GPI-anchor of GPI-ICAM1 either before incorporation (FIG. 5A) or after (FIG. 5B) incorporation was carried out. PI-PLC treatment of GPI-ICAM1 before incorporation and PI-PLC treatment of VLPs that have been incorporated with GPI-ICAM1 both led to decreased expression of ICAM1 on VLPs as detected by Western blotting to ICAM1, whereas when the PI-PLC inhibitors, $ZnCl_2$, or 1,10-phenanthroline, were included, expression was retained. To further confirm that incorporation occurs via the GPI-anchor, GPI-ICAM1 was incubated with 1% fatty-acid-free bovine serum albumin (BSA) or 1% orosomucoid that bind to the GPI-anchor before protein transfer in order to competitively inhibit incorporation of GPI-ICAM1 onto VLP membranes. FIG. 6 shows that GPI-ICAM1 incubated first with 1% BSA or 1% orosomucoid showed decreased incorporation onto VLPs compared to those incorporated without prior incubation with BSA or orosomucoid.

Figure 7:
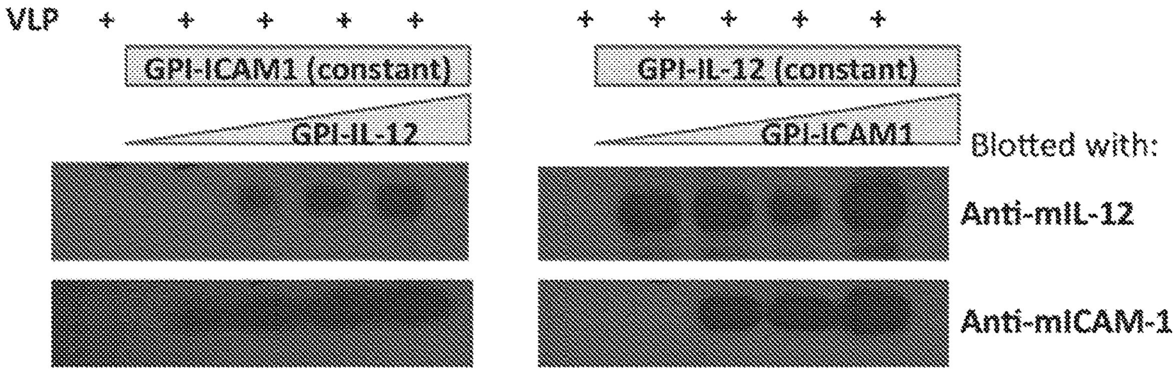
FIG. 7 shows data on the incorporation of two GPI-ISMs onto VLPs simultaneously.

Incorporation of More Than One GPI-Protein Simultaneously on the Same VLPs by Protein Transfer To determine if more than one GPI-protein could incorporate simultaneously onto the surface of VLPs by protein transfer, VLPs were incubated with GPI-ICAM1 and GPI-IL-12 simultaneously at 37° C. for 2 h. FIG. 7 shows that influenza VLPs can incorporate both GPI-ISMs on their surface and the expression of the first GPI-protein is not affected by the expression of the second GPI-protein.

Structural Integrity of VLPs Remains Intact After Protein Transfer.

Figure 8:
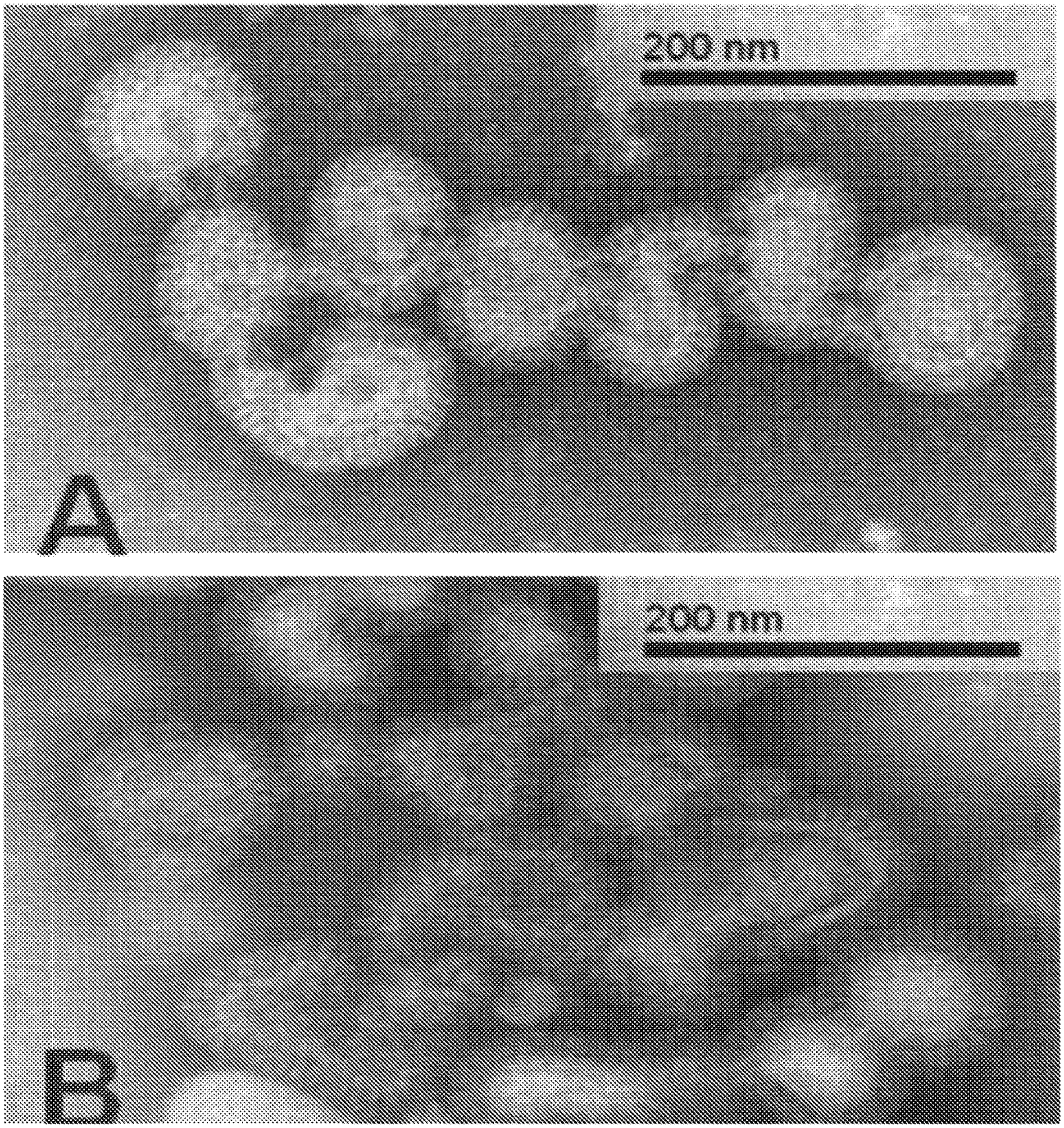
FIG. 8 shows a EM of VLPs (A) before and (B) after protein transfer with GPI-ICAM1.

To determine if the structural integrity of the VLPs remains intact after incorporation, electron microscopy of VLPs before and after incorporation was conducted. FIG. 8 shows that even after incorporation, the VLP membranes remain intact suggesting that the protein transfer method is not detrimental to the VLP structural integrity. This data show that purified GPI-proteins are able to incorporate onto influenza VLPs within 2 h at 37° C. via the GPI-anchor without disturbing the structural integrity of the VLPs.

Study Tumor Regression and Immune Responses Induced by Vaccination with VLPs Modified with GPI-HER-2 and GPI-ISMs by Protein Transfer in Mice with Established Tumors Protein transferred-VLPs that express the GPI-HER-2 in combination with GPIISMs, such as GPI-IL-2, GPI-IL-12, GPI-B7-1, and GPI-ICAM-1, leads to tumor regression in mice with established tumors that express HER-2. Although it is not intended that the disclosure be limited by any particular mechanism, the incorporation of cytokines onto the surface of VLPs allows for a slow release depot of the cytokines into the administered microenvironment, leading to increased activation of immune effector cells at the vaccination site while decreasing chances of systemic toxicity. Furthermore, the receptors of the ISMs, IL-2, IL-12, and ICAM-1 are found on APCs allowing for enhanced adhesion and activation of the APCs by the VLPs, thus leading to enhanced uptake and presentation. The receptors for IL-12 and B7-1 are also found on other immune cells such as NK cells and mast cells, allowing for the activation of a wide variety of immune effector cells to be elicited by the association of these ISMs onto the surface of VLPs. Since the immune response is directed against the antigens found on the VLPs, incorporating TAAs along with ISMs onto the surface of VLPs will direct the immune response towards the TAAs that are overexpressed on tumor cells as well.

To determine the efficacy of VLPs incorporated with GPI-TAAs and GPI-ISMs in regressing established tumors in vivo, one inoculates BALB/c mice with 4T07 tumor cells that expressing HER-2 and then start treatment a few days later (Table 1).

TABLE 1

Vaccination groups (n = 9)

| Group | Vaccination groups |
|---|---|
| 1 | PBS |
| 2 | VLP |
| 3 | VLP-GPI-HER-2 |
| 4 | VLP-GPI-HER-2 + GPI-IL-12 + GPI-IL-2 |
| 5 | VLP-GPI-HER-2 + GPI-IL-12 + GPI-IL-2 + GPI-B7-1 |
| 6 | VLP-GPI-HER-2 + GPI-IL-12 + GPI-IL-2 + GPI-B7-1 + GPI-ICAM-1 |
| 7 | VLP-GPI-IL-12 + GPI-IL-2 + GPI-B7-1 + GPI-ICAM-1 |

One injects live 4T07 tumor cells s.c. into the left flank of the mice and injects VLP in the right flank starting on days 4, 8, and 12 after tumor inoculation. If tumors do not regress, one uses a more vigorous 2-day interval immunization schedule. One monitors the mice daily and measures the size of the tumor. One screens for the production of antibodies to HER2/neu using flow cytometry or cell ELISA.

Expression of Human Breast Cancer Antigens in 4T07-WT Cells

Using the 4T07 murine breast cancer model the effects of expressing GPI-anchored immune stimulatory molecules (GPI-ISMs), namely cytokines (IL-2, IL-12) and the costimulatory protein B7-1, were investigated on the surface of the tumor cells. BALB/c mice were challenged subcutaneously (s.c.) with either wild-type 4T07 cells (4T07-WT) or 4T07 cells expressing GPI-ISMS. Significant splenomegaly was observed in the mice challenged with 4T07-WT cells relative to the mice challenged with 4T07 cells expressing GPI-ISMs. This observed splenomegaly correlated with tumor size and a 4-5 fold increase in the percentage of splenic CD11b+Gr1+ MDSCs indicating the role of active immune suppression in the tumorigenicity of 4T07 breast cancer cells. Studies were conducted to analyze the effect of GPI-ISMs on infiltrating cells into the tumor microenvironment as well as in the spleen and draining lymph nodes (dLNs). Three groups of mice were challenged (s.c.) with the following cells mixed in a 1:1 ratio with BD Matrigel™ (a solubilized basement membrane preparation derived from a mouse sarcoma): 4T07-WT, 4T07-B7/IL-12 or PBS (control). Seven days post challenge, the Matrigel/tumor, spleen and dLNs were harvested from the mice, digested and analyzed for cellular infiltrates by flow cytometry. The expression of GPI-ISMs on the surface of tumor cells led to reduced angiogenesis as evidenced by a reduced level of blood vessels and decreased presence of CD4+CD25+ FOXP3+ regulatory T cells and CD11b+Gr1+ MDSCs locally at the tumor site and dLNs as well as systemically in the spleen. Additionally, there was a decrease in CD8+PD1+ exhausted T cells at the tumor site. Along with the inhibition of immune suppressive cell populations, the GPI-ISMs increased the presence of CD4+ and CD8+ T cells as well as dendritic cells and B cells. These observations suggest that components of the active immune suppression evident in this model can be inhibited by expressing GPI-ISMs on the surface of the 4T07 tumor cells and could be effective in a therapeutic setting.

Figure 9:
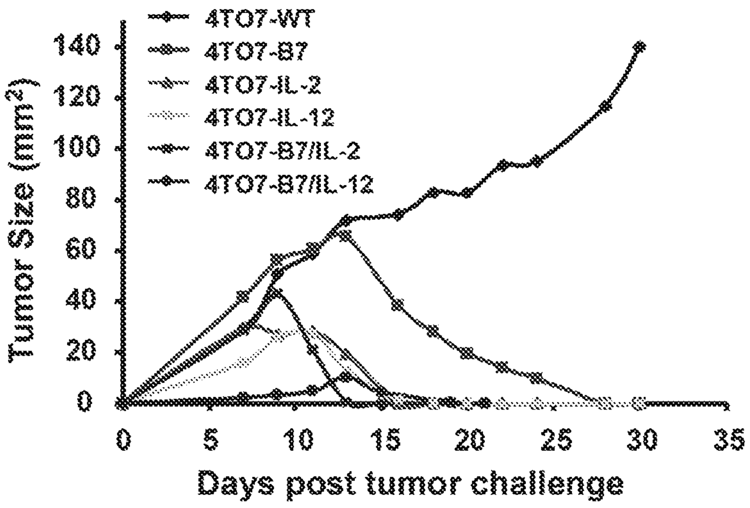
FIG. 9 shows data on the direct challenge with wild-type or GPI cytokine transfected 4T07 cells. BALB/C mice (n=5/group) were challenged s.c. in the hind flank with $2\times10^5$ cells in 100 μl PBS and were monitored every 2-3 days for tumor growth. Mean was calculated as the average of the tumor measurements from five mice per group. For the purpose of clarity, standard deviation was not included in the graph instead the values from individual mice in each group is given in FIG. 10.
Figure 10:
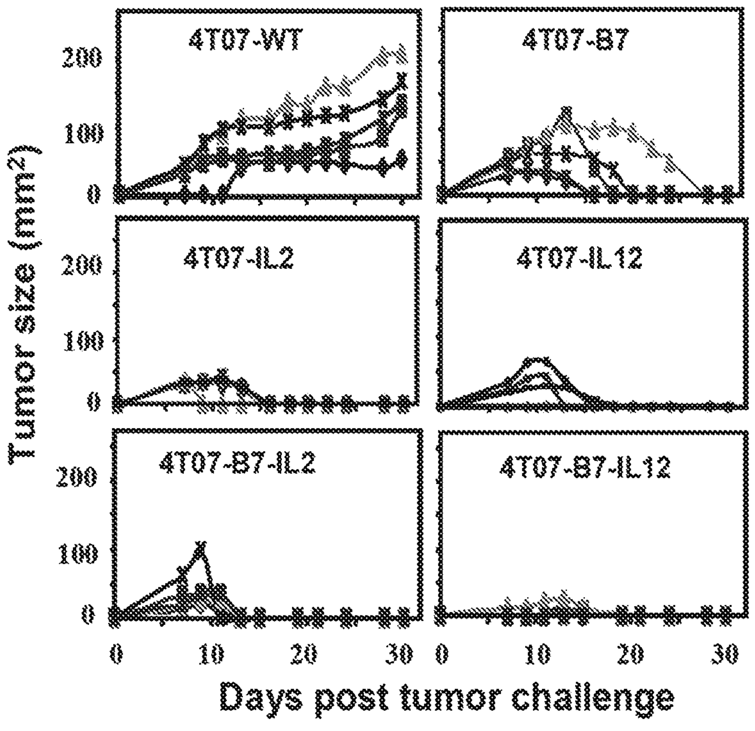
FIG. 10 shows tumor size in individual mice post direct challenge with wild-type or transfected 4T07 murine mammary tumor cells. BALB/C mice (n=5/group) were challenged s.c. in the hind flank with $2\times10^5$ cells in 100 μl PBS and were monitored every 2-3 days for tumor growth. Each data line represents an individual mouse per group.

BALB/C female mice (five per group) were challenged subcutaneously (s.c.) with wild-type 4T07 or transfected 4T07-B7, GPI-IL-2, GPI-IL-12, B7/GPI-IL-2 or B7/GPI-IL-12 cells (all $2\times10^5$ cells in 100 μl PBS). Mice were injected s.c. in the rear flank and were monitored daily. Tumor size was measured using Vernier calipers every 2nd-$3^{rd}$ day by taking 2×2 perpendicular measurements, and tumor size ($mm^2$) was calculated by multiplying the two diameters. Mice were euthanized when the tumor size reached close to 2 $cm^2$. After 33 days of the initial challenge, tumor-free mice in the experimental groups were rechallenged on the opposite hind flank with wild-type 4T07 cells (2×105 in 100 μl PBS). Mice in each group were marked individually by ear punch and tumor growth was measured and recorded for each mouse separately. The wild-type and transfected tumor cell lines all began to grow tumors in vivo, but while the wild-type tumors continued to increase in size, the tumors from the modified cell lines all regressed (See FIGS. 9 and 10).

Preparation and Evaluation of hHER-2(ECD)-CD59 GPI

Figure 11:
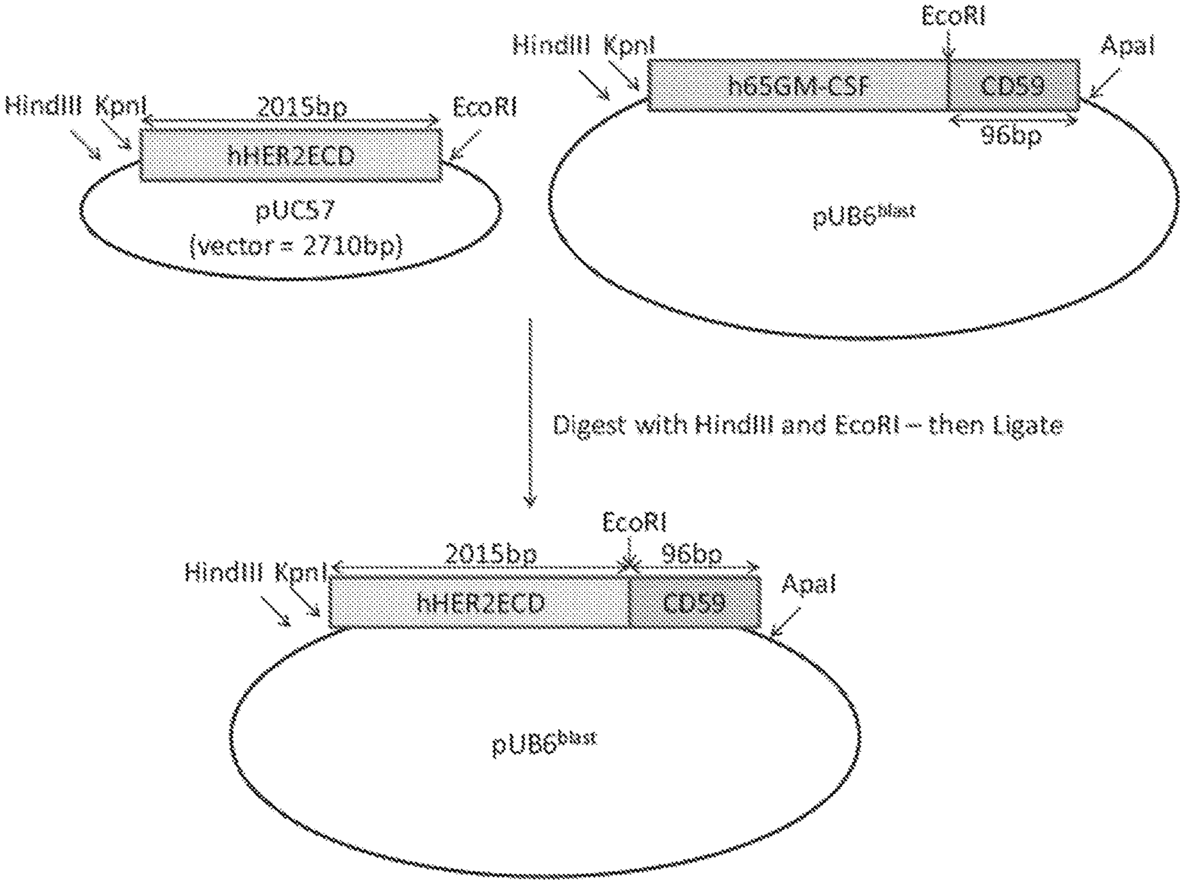
FIG. 11 illustrates the production of extracellular portion of hHER-2 (hHER-2ECD).

HER-2ECD is the extracellular portion of hHER-2. The hHER-2 extracellular domain with CD59 GPI signal sequence were join and introduced by a EcoRI site, i.e., joining region: g/aattc introduced EcoRV site (gat/atc) before sequence and ApaI (gggcc/c) site after sequence at the joining region as illustrated in FIG. 11. Before the sequence, an optimized IL-2 Kozak sequence along with the restriction enzyme sites HindIII and KpnI were added. Following the hHER2ECD sequence an EcoRI site is added. At base pair position 1365 of hHER2, a change in base pair from T was made to C in order to remove an EcoRI restriction enzyme site at this position, however, the final amino acid still remains as an isoleucine. (2015 bp). FIG. 12 shows flow cytometry analysis of CHO cells expressing GPI-human HER-2 (hHER-2-CD59) using TA1 mAb. Testing shows that HER-2 expressed in CHO cells is GPI-anchored. PIPLC is an enzyme which cleaves GPI anchor, reduces the level of expression. PI-PLC treated CHOK1-hHER-2ECD-CD59 cells reduced hHER-2 cell surface expression by 98.4%. PIPLC will not have any effect on normal HER-2.

Nucleic acid encoding the hHER-2 extracellular domain E (Amino Acids 22-652) and GPI-anchor signal sequence (SEQ ID NO: 7) AAGGGGAGGT AACCCTGGCC CCTTTGGTCG GGGCCCCGGG CAGCCGCGCG CCCCTTCCCA CGGGGCCCTT TACTGCGCCG CGCGCCCGGC CCCCACCCCT CGCAGCACCC CGCGCCCCGC GCCCTCCCAG CCGGGTCCAG CCG-GAGCCAT GGGGCCGGAG GATATC CCGCAGTGAG CACCATGGAG CTGGCGGCCT TGTGCCGCTG GGGGCTCCTC CTCGCCCTCT TGCCCCCCGG AGCCGCGAGC ACCCAAGTGT GCACCGGCAC AGA-CATGAAG CTGCGGCTCC CTGCCAGTCC CGA-GACCCAC CTGGACATGC TCCGCCACCT CTACCAGGGC TGCCAGGTGG TGCAGGGAAA CCTGGAACTC ACCTACCTGC CCACCAATGC CAGCCTGTCC TTCCTGCAGG ATATCCAGGA GGTGCAGGGC TACGTGCTCA TCGCTCACAA CCAAGTGAGG CAGGTCCCAC TGCAGAGGCT GCG-GATTGTG CGAGGCACCC AGCTCTTTGA GGACAAC-TAT GCCCTGGCCG TGCTAGACAA TGGAGACCCG CTGAACAATA CCACCCCTGT CACAGGGGCC TCCCCAGGAG GCCTGCGGGA GCTGCAGCTT CGAAGCCTCA CAGAGATCTT GAAAGGAGGG GTCTTGATCC AGCGGAACCC CCAGCTCTGC TACCAGGACA CGATTTTGTG GAAGGACATC TTC-CACAAGA ACAACCAGCT GGCTCTCACA CTGATA-GACA CCAACCGCTC TCGGGCCTGC CACCCCTGTT CTCCGATGTG TAAGGGCTCC CGCTGCTGGG GAGAGAGTTC TGAGGATTGT CAGAGCCTGA CGCGCACTGT CTGTGCCGGT GGCTGTGCCC GCTGCAAGGG GCCACTGCCC ACTGACTGCT GCCATGAGCA GTGTGCTGCC GGCTGCACGG GCCCCAAGCA CTCTGACTGC CTGGCCTGCC TCCACTTCAA CCACAGTGGC ATCTGTGAGC TGCACTGCCC AGCCCTGGTC ACCTACAACA CAGACACGTT TGAGTCCATG CCCAATCCCG AGGGCCGGTA TACATTCGGC GCCAGCTGTG TGACTGCCTG TCCCTACAAC TACCTTTCTA CGGACGTGGG ATCCTGCACC CTCGTCTGCC CCCTGCACAA CCAAGAGGTG ACAGCAGAGG ATG-GAACACA GCGGTGTGAG AAGTGCAGCA AGCCCTGTGC CCGAGTGTGC TATGGTCTGG GCATGGAGCA CTTGCGAGAG GTGAGGGCAG TTACCAGTGC CAATATCCAG GAGTTTGCTG GCTGCAAGAA GATCTTTGGG AGCCTGGCAT TTCTGCCGGA GAGCTTTGAT GGGGACCCAG CCTC-CAACAC TGCCCCGCTC CAGCCAGAGC AGCTC-CAAGT GTTTGAGACT CTGGAAGAGA TCACAGGTTA CCTATACATC TCAGCATGGC CGGACAGCCT GCCTGACCTC AGCGTCTTCC AGAACCTGCA AGTAATCCGG GGACGAATTC TGCACAATGG CGCCTACTCG CTGACCCTGC AAGGGCTGGG CATCAGCTGG CTGGGGCTGC GCT-CACTGAG GGAACTGGGC AGTGGACTGG CCCT-CATCCA CCATAACACC CACCTCTGCT TCGTGCACAC GGTGCCCTGG GACCAGCTCT TTCG-GAACCC GCACCAAGCT CTGCTCCACA CTGC-CAACCG GCCAGAGGAC GAGTGTGTGG GCGAGGGCCT GGCCTGCCAC CAGCTGTGCG CCCGAGGGCA CTGCTGGGGT CCAGGGCCCA CCCAGTGTGT CAACTGCAGC CAGTTCCTTC GGGGCCAGGA GTGCGTGGAG GAATGCCGAG TACTGCAGGG GCTCCCCAGG GAGTATGTGA ATGCCAGGCA CTGTTTGCCG TGCCACCCTG AGTGTCAGCC CCAGAATGGC TCAGTGACCT GTTTTGGACC GGAGGCTGAC CAGTGTGTGG CCTGTGCCCA CTATAAGGAC CCTCCCTTCT GCGTGGCCCG CTGCCCCAGC GGTGTGAAAC CTGACCTCTC CTACATGCCC ATCTGGAAGT TTCCA-GATGA GGAGGGCGCA TGCCAGCCTT GCCCCAT-CAA CTGCACCCAC TCCTGTGTGG ACCTGGATGA CAAGGGCTGC CCCGCCGAGC AGAGAGCCAG CCCTCTGACG GAATTC CTTGAAAATG GTGGGA-CATC CTTATCAGAG AAAACAGTTC TTCTGCTGGT GACTCCATTT CTGGCAGCAG CCTGGAGCCT TCATCCCTAA CAGAAGGCCA AGGGGCCCTCCG.

The invention claimed is:

1. A method of treating metastatic head and neck squamous cell carcinoma (HNSCC) comprising administering an effective amount of HNSCC tumor membrane vesicles (TMVs) in combination with an anti-PD-1 antibody to a subject in need thereof, wherein the TMVs comprise:

A B7-1 molecule anchored to a lipid membrane on the exterior of the TMVs;

And

An IL-12 anchored to the lipid membrane on the exterior of the TMVs.

2. The method of claim 1, wherein the anti-PD-1 antibody is nivolumab.

3. The method of claim 1, wherein the TMVs further comprise a HER-2 anchored to the lipid membrane on the exterior of the TMVs.

4. The method of claim 3, wherein the HER-2 is encoded by a nucleic acid comprising SEQ ID NO:7.

5. The method of claim 1, wherein one or more of the B7-1 and IL-12 is anchored to the lipid membrane through a conjugated glycosyl-phosphatidylinositol.

6. The method of claim 1, wherein both the B7-1 and IL-12 are anchored to the lipid membrane through a conjugated glycosyl-phosphatidylinositol.

* * * * *